(12) United States Patent
Cherepinsky et al.

(10) Patent No.: US 7,858,301 B2
(45) Date of Patent: Dec. 28, 2010

(54) METHOD OF PROBE DESIGN FOR NUCLEIC ACID ANALYSIS BY MULTIPLEXED HYBRIDIZATION

(75) Inventors: Vera Cherepinsky, Sandy Hook, CT (US); Bhubaneswar Mishra, Great Neck, NY (US); Ghazala Hashmi, Holmdel, NJ (US); Michael Seul, Fanwood, NJ (US)

(73) Assignee: Bioarray Solutions, Ltd., Warren, NJ (US)

( * ) Notice: Subject to any disclaimer, the term of this patent is extended or adjusted under 35 U.S.C. 154(b) by 747 days.

(21) Appl. No.: 10/841,931

(22) Filed: May 7, 2004

(65) Prior Publication Data

US 2005/0250115 A1    Nov. 10, 2005

Related U.S. Application Data

(60) Provisional application No. 60/468,839, filed on May 7, 2003.

(51) Int. Cl.
*C12Q 1/68* (2006.01)
*C07H 21/02* (2006.01)
*C07H 21/04* (2006.01)

(52) U.S. Cl. .................... 435/6; 536/23.1; 536/24.3

(58) Field of Classification Search ............. None
See application file for complete search history.

(56) References Cited

U.S. PATENT DOCUMENTS 6,355,419 B1 *   3/2002   Alfenito ................. 435/6
7,060,431 B2 *   6/2006   Chee et al. ............. 435/6
7,132,239 B2 *  11/2006   Livak et al. ............. 435/6

OTHER PUBLICATIONS

SantaLucia, J. Jr., PNAS USA, vol. 95, pp. 1460-1465 (1998).*
Breslauer, K.J. et al., PNAS USA, vol. 83, pp. 3746-3750 (1986).*
Relogio, A. et al., Nucl. Acids Res., vol. 30,e51, pp. 1-10 (2002).*
Chee, M. et al., Science, vol. 274, pp. 610-613 (1996).*
Cherepinsky, Vera, "On mathematical aspects of genomic analysis", Ph.D. Thesis, published Mar. 2004.*
Thesis Chapter: "Competitive Hybridization: Physical Model" by V. Cherepinsky; Mar. 26, 2004.

* cited by examiner

*Primary Examiner*—Teresa E Strzelecka
(74) *Attorney, Agent, or Firm*—Womble Carlyle Sandridge & Rice, PLLC

(57) ABSTRACT

Disclosed is an analysis method useful in multiplexed hybridization-mediated analysis of polymorphisms, i.e., wherein a labeled nucleic acid of interest ("target") interacts with two or more pairs of immobilized degenerate capture probes. In one embodiment, one member of each pair has a sequence that is complementary to the normal ("wild-type") sequence in a designated location of the target, while the other member of each pair has a sequence that is complementary to an anticipated variant ("mutant" or "polymorph") sequence in that location of the target. These methods permit selection of two or more probe pairs such that, for each pair of probes interacting with a given target strand, interaction of the target with a preferred member of the probe pair is optimized. Also interpreting results obtained by multiplexed hybridization of the target to two or more pairs of probes under conditions permitting competitive hybridization is disclosed.

3 Claims, 13 Drawing Sheets

| | Probe SEQUENCES |
|---|---|
| A327-PM | AGT TCT TGG AGA AGG TG (SEQ. ID NO.:3) |
| A327-MM | AGT TCT TTG AGA AGG TG (SEQ. ID NO.:4) |
| C-381-PM | TTA TTC ACC TTG CTA AA (SEQ. ID NO.:5) |
| C-381-MM | TTA TTC ACG TTG CTA AA (SEQ. ID NO.:6) |
| B-354-PM | GAG TGG AGG TCA ACG AG (SEQ. ID NO.:7) |
| B-354-MM | GAG TGG AGA TCA ACG AG (SEQ. ID NO.:8) |
| D-359-PM | GAG GTC AAC GAG CAA GA (SEQ. ID NO.:9) |
| D-359-MM | GAG GTC AAT GAG CAA GA (SEQ. ID NO.:10) |
| E-286-PM | TGG TAA TAG GAC ATC TC (SEQ. ID NO.:11) |
| E-286-MM | TGG TAA TAA GAC ATC TC (SEQ. ID NO.:12) |

FIG. 6A

| PROBE | $K_{PM}$ | $K_{MM}$ | $K_{PM}/K_{MM}$ |
|---|---|---|---|
| A327 | $1.3 \times 10^6$ | $2.6 \times 10^4$ | 47.8 |
| D359 | $1.1 \times 10^7$ | $1.6 \times 10^5$ | 65.19 |
| C381 | $3.9 \times 10^4$ | $1.0 \times 10^3$ | 38.4 |

FIG. 6B

Δ PLOT FOR PROBE C381

| PROBE | WT/M IN PRESENCE OF | | | | |
|---|---|---|---|---|---|
| | A327 | B354 | C381 | D359 | E241 |
| A327 | 3.5 | 11 | 13.8 | 11 | NA |
| B354 | 10.9 | 10.9 | 10.9 | 10.9 | 9.2 |
| C381 | 40.3 | 40.3 | 40.3 | 40.3 | NA |
| D359 | 203 | 203 | 203 | 203 | 166 |
| E241 | NA | 14.3 | 14.3 | NA | 14.3 |
FIG. 9A
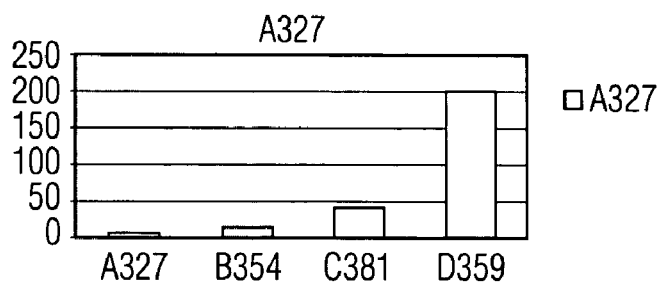
FIG. 9B
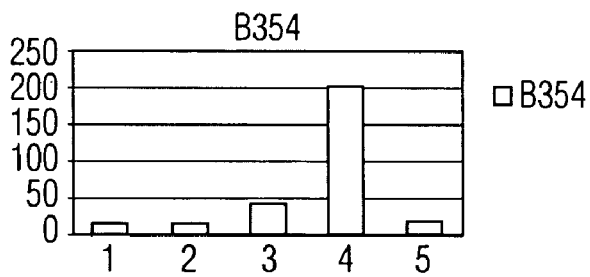
FIG. 9C
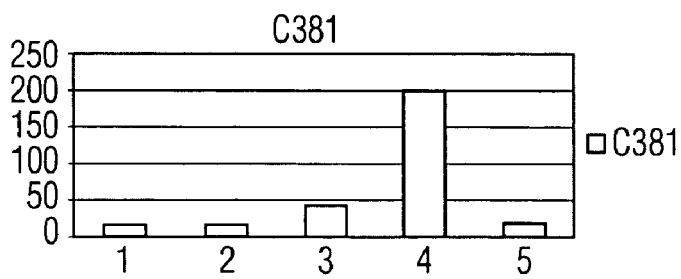
FIG. 9D
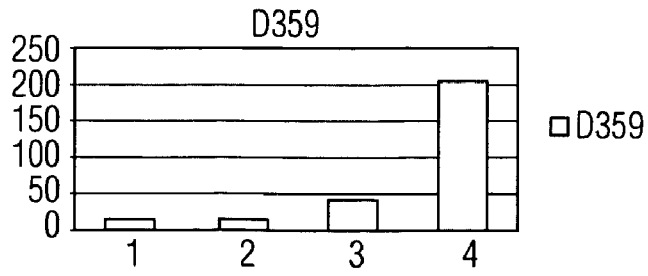
FIG. 9E

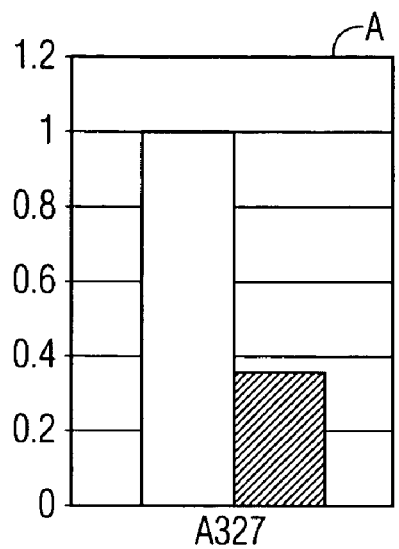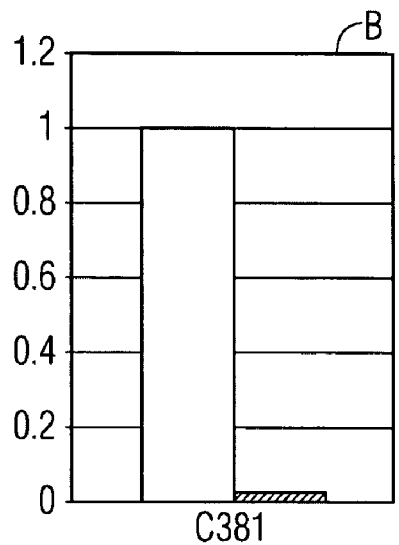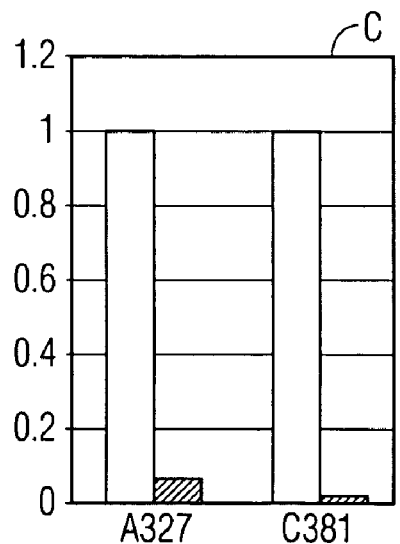
FIG. 10A

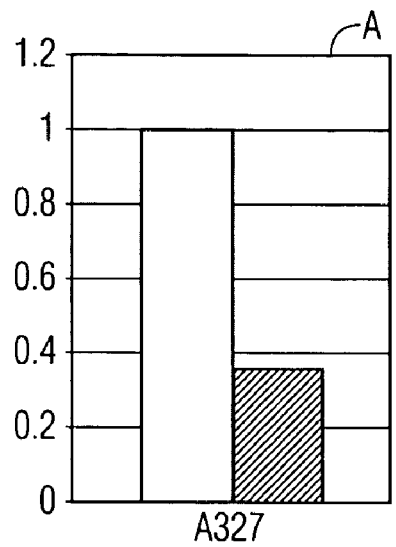
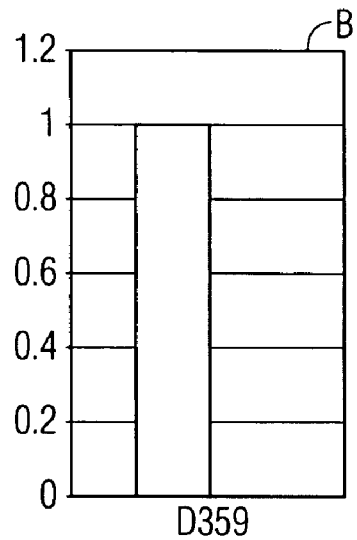
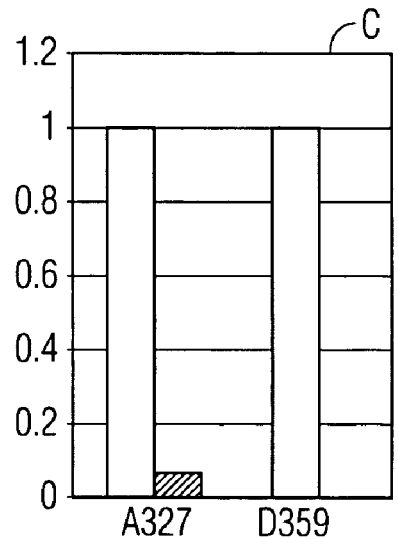
FIG. 10B

METHOD OF PROBE DESIGN FOR NUCLEIC ACID ANALYSIS BY MULTIPLEXED HYBRIDIZATION

RELATED APPLICATIONS

This application claims priority to U.S. Provisional Application No. 60/468,839, filed May 7, 2003.

BACKGROUND

Recently, multiplexed methods have been developed suitable for genome analysis, detection of polymorphisms, molecular karyotyping, and gene-expression analysis, where the genetic material in a sample is hybridized with a set of anchored oligonucleotide probes. Understanding the results, displayed when labeled subsequences in the target bind to particular probes, is based on decoding the probe array to determine the sequence of the bound members.

Embodiments of such arrays include spatially encoded oligonucleotide probe arrays, where the array is placed on a chip and particular probes are placed in designated regions of the chip. Also included are particle or microbead arrays, designated random encoded arrays, where the oligonucleotide probes are bound to encoded beads, and where the encoding identifies the probe bound thereto. See, e.g., U.S. application Ser. No. 09/690,040 Such arrays allow one to conduct high-throughput multiplexed hybridization involving thousands of probes on a surface.

One problem in multiplexed analysis is in interpreting the results. In a conventional multiplexed "reverse dot blot" hybridization assay, the target oligonucleotide strands are labeled, and the labeling is detected, post-hybridization to the probe array, to ascertain binding events. The reliability of the final computational interpretation of the data depends on understanding the errors due to unintended interactions among targets and probes, as probes and targets are multiplexed.

The standard approach to the thermodynamic analysis of nucleic acid hybridization invokes interactions between adjacent ("nearest-neighbor") base-pairs to account for the thermodynamic stability of the duplex under given experimental conditions including temperature, ionic strength, and pH (see, e.g., Cantor & Smith, "Genomics", Wiley Interscience, 1999). A variety of commercial software packages for probe and primer design invoke this model to estimate the thermodynamic stability, or equivalently, the "melting temperature", $T_m$, usually defined as the temperature at which half of a given number of nucleic acid duplexes have separated into single strands—a phenomenon also referred to as "denaturing" or "de-annealing." The melting temperature of a probe or primer—more precisely, the duplex formed by the probe or primer and a complementary single oligonucleotide strand—represents the single most widely used parameter to guide the design of probes and primers in assays involving hybridization. Many commercial software packages are available for this purpose, e.g., OLIGO, VISUALOMP, PRIMERSELECT, ARRAY DESIGNER, PRIMER3, and others.

Duplex stability is significantly affected by the presence of mismatched bases, so that even a single point mutation can substantially lower the melting temperature (FIG. 1). This phenomenon provides the basis for the standard method of detecting such a mutant or polymorph in a designated location within a target sequence using hybridization analysis: a pair of probes, one member complementary to the normal target composition at the designated location, the other complementary to an anticipated variant, are permitted to interact with the target. For example, in a "reverse dot blot" or READ™ assay format, both probes are immobilized and permitted to capture a portion of a labeled target molecule of interest that is placed in contact with the probes. It is the objective of such an analysis to optimize discrimination between the signal associated with the "perfectly matched (PM)" probe having the sequence that is perfectly matched to the target sequence and the signal associated with the "mismatched (MM)" probe having the sequence that deviates from that of the target sequence in the designated location. It is desirable for the signal intensity to indicate the amount of captured target; an example would be target-associated fluorescence, where a higher intensity signal indicates more capture. For a single pair of PM/MM probes, optimal discrimination would be ensured by selecting the temperature to fall between the respective melting temperatures, $T_m^{PM}$ and $T_m^{MM} < T_m^{PM}$ of perfectly matched and mismatched probes (FIG. 1). However, in multiplexed reactions, involving two or more PM/MM probe pairs, no such choice of a single temperature generally will be possible. In addition, multiplexed mutation analysis generally has to account for the possibility of cross-hybridization between other than cognate probes and targets, a possibility that exists whenever probes or targets display a sufficiently high degree of homology so as to interact with sufficient strength so as to stabilize a duplex under given experimental conditions.

Another source of error arises from competitive hybridization, where a target consists of possibly two distinct subsequences mA and mB, which can be characterized by separately hybridizing the target with either a mixture of specific probes pmA and control probes mmA, or a mixture of specific probes pmB and control probes mmB, respectively. In either case the ratio of specific signal to the control signal, obtained from each separate experiment, indicates how often either message is present. On the other hand, contrary to one's expectations, if the two messages were queried by ratios of the respective signals in a multiplexed experiment consisting of all four probes pmA, mmA, pmB, and mmB, one finds these ratios to differ from their values in the earlier experiments and by amounts that cannot simply be explained by the statistical noise. In particular, if one of the ratio values decreases severely, the resulting false negative errors can become significant enough to affect the multiplexed assay results. The negative effects can worsen as the number of multiplexed probes for a target increases.

There is a need for a method to correct for such errors, and also for assay design methods and probe selection, which will avoid or minimize such errors.

SUMMARY

The analysis method disclosed herein is useful in multiplexed mutation analysis or, more generally, in hybridization-mediated multiplexed analysis of polymorphisms under conditions permitting competitive hybridization, i.e., wherein single strands of a labeled nucleic acid of interest ("target") interact with two or more pairs of immobilized degenerate capture probes. In one embodiment, one member of each pair has a sequence that is complementary to the normal ("wild-type") sequence in a designated location of the target, while the other member of each pair has a sequence that is complementary to an anticipated variant ("mutant" or "polymorph") sequence in that location of the target. The methods herein permit the selection of two or more probe pairs such that, for each pair of probes interacting with a given target strand, the interaction of the target with a preferred member of the probe pair is optimized.

Also disclosed is: (i) a method of interpreting results obtained by multiplexed hybridization of the target to two or more pairs of probes under conditions permitting competitive hybridization; and (ii) application of these methods of probe selection and interpretation to multiplexed analysis of target strands involving the use of enzyme-catalyzed elongation reactions such as the polymerase chain reaction. Preferably, in mutation analysis, the amount of duplex formed for each probe is determined by recording an optical signature ("signal") associated with the encoded bead displaying that probe such that the intensity of the optical signature is proportional to the amount of duplex formed. That is, probes are analyzed in pairs, with one member complementary to the normal sequence and the other to the variant, i.e., the mutant or polymorph. One method of analyzing the respective results is to determine the ratio of the signals generated from mutant hybridizations and that from wild-type hybridizations, and to set relative ranges of values indicative of normal, heterozygous variant, and homozygous variant.

The paired sequences often will differ by only one nucleotide, and therefore, some degree of cross-hybridization is anticipated upon introduction of normal and variant samples. This can reduce discrimination in signal, even where one is examining signal ratios.

The methods herein invoke a model of mass action in which a target, T, present at initial concentration, t, forms a hybridization complex ("duplex"), C, at concentration or lateral density, c, with immobilized probes, P, present at a concentration or lateral density, p, in accordance with the relation c=Kpt in which K denotes an affinity constant that sets the scale of the strength of interaction between probe(s) and target(s). In a preferred embodiment, K represents a sequence-specific quantity which is evaluated as described herein using standard methodology well-known in the art (see SantaLucia, PNAS USA 95, 1460-1465 (1998)) by invoking certain thermodynamic parameters relating to the strength of base-pairing interactions that mediate the formation of a duplex.

These methods also guide the selection of two or more probe pairs so as to maximize, for each pair of probes interacting with a given target strand, the ratio of a first intensity, $I^{PM}$, indicating the amount of duplex formed between target and perfectly matched ("PM") probe and a second intensity, $I^{MM}$, indicating the amount of duplex formed between target and mismatched ("MM") probe in a pair of probes.

Also disclosed is a method for the correction of results following hybridization of the target to sets of PM/MM pairs of probes (also herein meant to include sets of "degenerate" probes) under conditions permitting competitive hybridization.

The probes and methods disclosed herein were extensively validated in many patient samples, and demonstrated as capable of diagnosing CF.

BRIEF DESCRIPTION OF THE DRAWINGS

FIG. 6A shows sequences of PM and MM capture probes A327, B354, C381, D359, and E286, designed for the hybridization-mediated detection of mutations in exon 11 of the CFTR gene.

FIG. 6B shows the affinity constants for the probes A327, D359, and C381.

FIG. 9A is a table showing the possible target-probe interactions of FIGS. 9B-9E.

FIGS. 9B to 9E show the results of wild type and mutant targets in the presence of five capture probes to regions of the exon 11 of the cystic fibrosis transmembrane regulator (CFTR) gene, referred to as A327, B354, C381, D359, and E286.

FIGS. 10A and 10B show the results of combinations of probes, as indicated in the figures.

DETAILED DESCRIPTION

Duplex Formation in Multiconstituent Reactions

Figure 1:
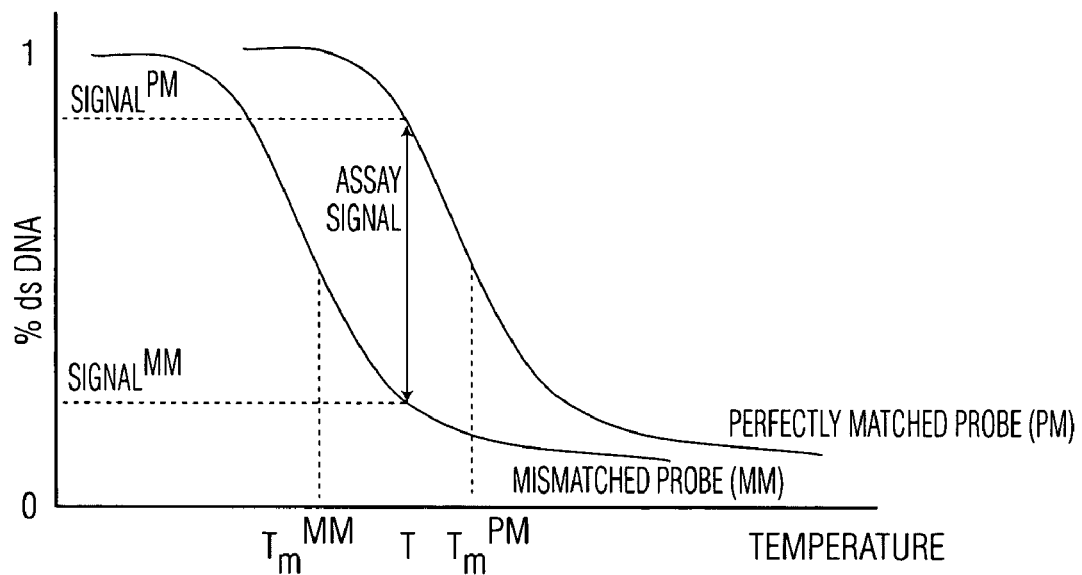
FIG. 1 shows a "melting" curve for a pair of PM and MM probes using the percentage of hybridization complex ("duplex") remaining as the order parameter; a mismatch results in a reduction of the melting temperature.
Figure 1A:
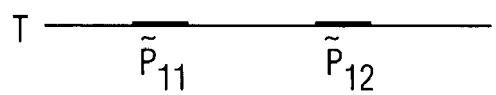
FIG. 1A depicts a target T with a single region perfectly complementary to probe $P_{11}$, and another region perfectly complementary to probe $P_{12}$.

To provide a basis for the quantitative description of competitive hybridization, one invokes a specific model of competitive hybridization involving the interaction of two or more PM/MM pairs of probes with the same target sequence. In such model, the array includes microbeads with probes attached, and the bead sizes are relatively large compared to the size of the probes. One assumes in this model that there are thousands of copies of the same probe attached to a single bead, and that the beads are spaced on a planar surface far enough apart in order to ensure that a single target strand may only hybridize to probes on a single bead. Thus, this assumption implies that the only possible complexes involve one target and one probe. The targets are obtained from a longer DNA, by PCR amplification with two primers to select clones of a region that are subjected to further characterization. Let T be a target with a single region perfectly complementary to probe $P_{11}$ and another region perfectly complementary to probe $P_{12}$ (see FIG. 1A). Let $P_{01}$ differ from $P_{11}$ in one base (i.e., the Hamming distance between $P_{01}$ and $P_{11}$ equals to 1, $H(P_{01}; P_{11})=1$). If $P_{11}$ and $P_{01}$ are the only probes present, we can expect that when we compare the concentration of the $P_{11}$ probes bound to T (denoted $[TP_{11}]$) to the concentration of the $P_{01}$ probes bound to T (denoted $[TP_{01}]$) the resulting ratio to be large, i.e.:

$$\frac{[TP_{11}]}{[TP_{01}]} \gg 1,$$

since their free energies are chosen to satisfy:

$$\Delta G(P_{01}) < \Delta G(P_{11})$$

$P_{01}$ clearly "competes" with $P_{11}$ for the target T. Consider yet another probe, $P_{02}$, that differs from $P_{11}$ in one base as well ($H(P_{11}; P_{02})=1$), but at a location different from the one in $P_{01}$ ($H(P_{01}; P_{02})=2$). Then $P_{02}$ also competes with $P_{11}$, but not as much with $P_{01}$, since $H(P_{01}; P_{02})=2$. Thus, in the presence of $P_{02}$, we expect $$\frac{[TP_{11}]}{[TP_{01}]}$$

to decrease, since $[TP_{01}]$ does not decrease much, but $[TP_{11}]$ does. However, in the presence of all four probes $P_{11}, P_{01}, P_{12}$, and $P_{02}$, the analysis of the resulting "mutual competitions" poses a non-trivial problem.

Figure 2:
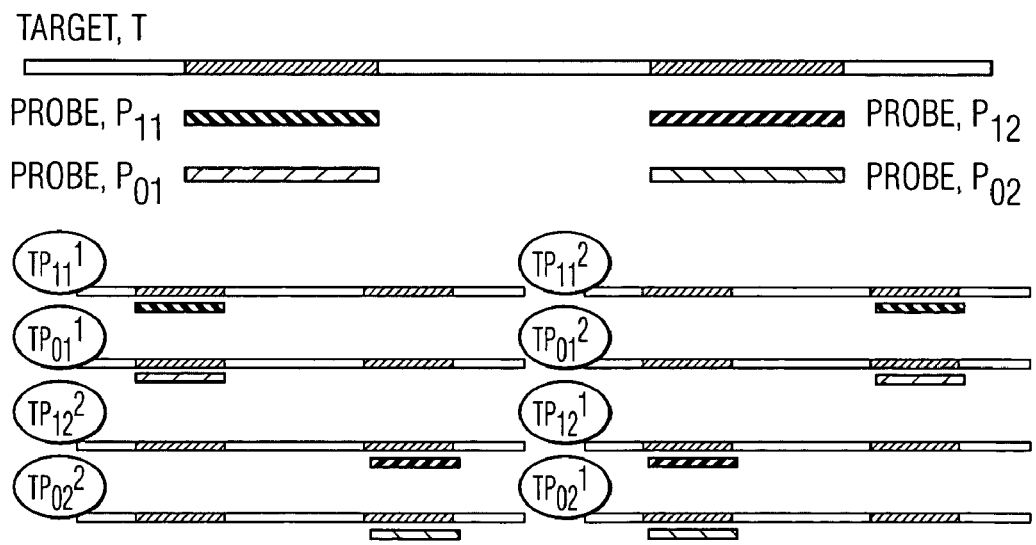
FIG. 2 depicts competitive hybridization between multiple probes and a single target.
Figure 3:
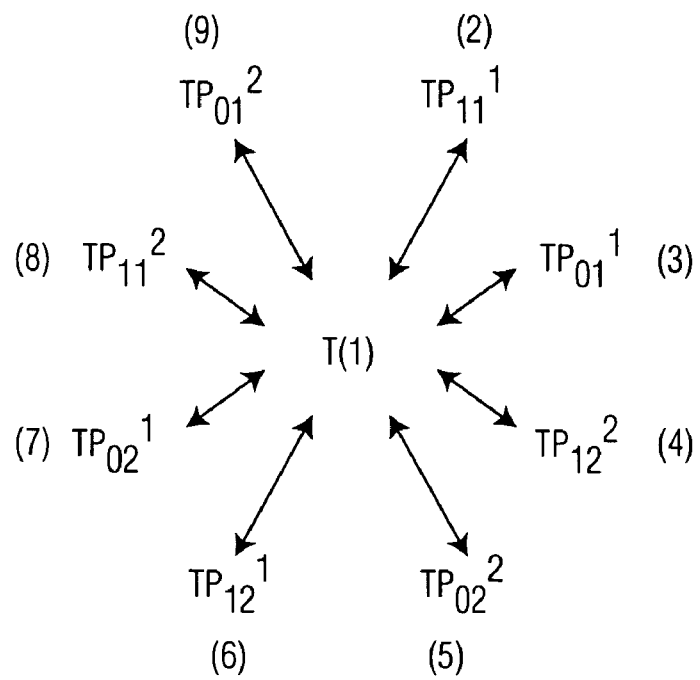
FIG. 3 shows a state transition diagram for the possible interactions of two PM/MM probe pairs and a target, T, where the target exists in one of 9 possible states: free target T, and bound target states $TP_{ij}^k$, where k=1, 2 is the binding site, j=1, 2 is the probe index, and i=1 for matched probe or 0 for mismatched probe. Cross-terms j≠k have lower affinity constants.

FIG. 2 depicts the competitive hybridization among probes for a target T with two sites each of which is complementary ("perfectly matched") to a particular probe: $P_{11}$ and $P_{12}$, respectively, and also where mismatched probes are included ($P_{01}$ and $P_{02}$, respectively). FIG. 3 depicts the state transition diagram for the interaction of the probes and the target in FIG. 2. For the sake of providing concrete predictions, nearest-neighbor ("NN") model of thermodynamic duplex stability is used to evaluate sequence-specific affinities, K, of probe-target complexes.

Nearest-Neighbor Model

The model of hybridization discussed so far treats the dynamics in terms of kinetic mass-action reactions and ignores both the mixing properties of the molecules and the exact physics of hybridization except for simply acknowledging that the thermodynamics parameters depend on base-pair composition. However, the process of hybridization actually involves the formation of base pairs between Watson-Crick-complementary bases. Namely, base pairing of two single stranded DNA molecules is determined by the fact that A (adenine) is complementary to T (thymine), and C (cytosine) is complementary to G (guanine). Such base pairing is due to the formation of hydrogen bonds between the complementary bases; thus, this interaction is characterized primarily by the composition of the interacting strands. Another physical interaction, base stacking, characterizes the hybridization process, and it has been shown to depend on the sequence rather than the composition of the strands. As base stacking depends on short-range interactions, it is thought to be adequately described by the Nearest-Neighbor (NN) model.

In the NN model, it is assumed that the stability of a given base pair is determined by the identity and orientation of the neighboring base pairs. Thus, each thermodynamic parameter of the hybridization process, such as the change in enthalpy ($\Delta H$), entropy ($\Delta S$), and free energy ($\Delta G$), is calculated as a sum of the contributions from each nearest-neighbor pair along a strand, corrected by some symmetry and initiation parameters. As the enthalpy and entropy terms may be assumed to be independent of temperature, they can be computed as follows:

$$\Delta H = \sum_x \Delta H_x + \Delta H(\text{init}) + \Delta H(\text{sym})$$

$$\Delta S = \sum_x \Delta S_x + \Delta S(\text{init}) + \Delta S(\text{sym})$$

where the terms $\Delta H_x$ and $\Delta S_x$ are tabulated for all ten possible NN dimer duplexes, as are the initiation and symmetry terms. The free energy computation is analogous:

$$\Delta G = \sum_x \Delta G_x + \Delta G(\text{init}) + \Delta G(\text{sym})$$

with the initiation and symmetry terms tabulated. The values $\Delta G_x$ for the dimer duplexes have been tabulated previously and reported at 25° C. (see Breslauer, et al., "Predicting DNA Duplex Stability from the Base Sequence," *PNAS USA* 83: 3746-3750, 1986) and at 37° C. (SantaLucia, J. Jr. "A Unified View of Polymer, Dumbbell, and Oligonucleotide DNA Nearest-neighbor Thermodynamics," *PNAS USA* 95:1460-1465, 1998). Since $\Delta G$ depends on the temperature, the values $\Delta G_x$ for the dimer duplexes can be easily calculated from the corresponding $\Delta H_x$ and $\Delta S_x$ parameters by:

$$\Delta G_x(T) = \Delta H_x - T\Delta S_x$$

The ten distinct dimer duplexes arise as follows. Following the notation of Breslauer et al., supra, each dimer duplex is denoted with a "slash-sign" separating antiparallel strands, e.g., AG/TC denotes 5'-AG-3' Watson-Crick base-paired with 3'-TC-5'. Table 1 below lists all sixteen ($=|\{A, T, C, G\}|^2=4^2$) possible dimers, identifying the equivalent ones.

TABLE 1

| $\frac{AA}{TT}$ | $\frac{AC}{TG} \equiv \frac{GT}{CA}$ | | $\frac{AG}{TC} \equiv \frac{CT}{GA}$ | | $\frac{AT}{TA}$ |
|---|---|---|---|---|---|
| $\frac{CA}{GT}$ | $\frac{CC}{GG} \equiv \frac{GG}{CC}$ | | $\frac{CG}{GC}$ | | $\frac{CT}{GA}$ |
| $\frac{GA}{CT}$ | $\frac{GC}{CG}$ | | | $\frac{GG}{CC}$ | $\frac{GT}{CA}$ |
| $\frac{TA}{AT}$ | $\frac{TC}{AG} \equiv \frac{GA}{CT}$ | $\frac{TG}{AC} \equiv \frac{CA}{GT}$ | | $\frac{TT}{AA} \equiv \frac{AA}{TT}$ | |

Since these simulations involve oligonucleotide probes, the parameters for the initiation of duplex formation used drawn from the results in the 1998 paper of SantaLucia, supra. There, two different initiation parameters were introduced to account for the differences between duplexes with terminal A-T and duplexes with terminal G-C. The additional "symmetry" parameter accounts for the maintenance of the C2 symmetry of self-complementary duplexes. The table of parameters used in these simulations, drawn from SantaLucia, supra, is duplicated in Table 2 below for convenience.

TABLE 2

NN Parameters at 1M NaCl. ΔG is calculated at 37° C.

| Interaction | ΔH kcal/mol | ΔS cal/K · mol | ΔG kcal/mol |
|---|---|---|---|
| AA/TT | −7.9 | −22.2 | −1.00 |
| AT/TA | −7.2 | −20.4 | −0.88 |
| TA/AT | −7.2 | −21.3 | −0.58 |
| CA/GT | −8.5 | −22.7 | −1.45 |
| GT/CA | −8.4 | −22.4 | −1.44 |
| CT/GA | −7.8 | −21.0 | −1.28 |
| GA/CT | −8.2 | −22.2 | −1.30 |
| CG/GC | −10.6 | −27.2 | −2.17 |
| GC/CG | −9.8 | −24.4 | −2.24 |
| GG/CC | −8.0 | −19.9 | −1.84 |
| Init. w/term. G · C | 0.1 | −2.8 | 0.98 |
| Init. w/term. A · T | 2.3 | 4.1 | 1.03 |
| Symmetry correction | 0 | −1.4 | 0.43 |

The following example illustrates how the free energy can be computed according to the formula above, using the values from Table 2.

```
5' C–G–A–A–G–T 3'        (SEQ ID NO.: 1)
   * * * * * *
3' G–C–T–T–C–A 5'        (SEQ ID NO.: 2)
```

$$\Delta G = \Delta G(CG/GC) + \Delta G(GA/CT) + \Delta G(AA/TT) + \Delta G(AG/TC) +$$
$$\Delta G(GT/CA) + \Delta G(\text{init. } w/G \cdot C) + \Delta G(\text{init. } w/A \cdot T) + 0$$
$$= -2.17 - 1.30 - 1.00 - 1.28 - 1.44 + 0.98 + 1.03$$
$$= -5.18 \text{ kcal/mol}$$

Since the duplex is not self-complementary, ΔG(sym)=0.

Affinity Constants

At equilibrium, the affinity constants $K_i^j$ are given by the formula:

$$K_i^j = \exp[-\Delta G/RT],$$

and ΔG due to stacking interactions is calculated as above. Other models may be possible or desirable and may be readily incorporated as a module into the computations performed by methods described herein.

A mathematical model to analyze the dynamics involved in a system like the one above is described below. As before, the assumption is that the steric effects prevent multiple probes from hybridizing to a single target strand (as probes are bound to large beads).

As shown in FIG. 3, one may observe a target strand T in one of the following nine possible states:

(1) T (Target is unbound.)

(2) $TP_{11}^1$; (3) $TP_{01}^1$; (4) $TP_{12}^2$; (5) $TP_{02}^2$ (Target is bound by "specific" hybridization.)

(8) $TP_{11}^2$; (9) $TP_{01}^2$; (6) $TP_{12}^1$; (7) $TP_{02}^1$ (Target is bound by "non-specific" hybridization.)

Bound target states have form $TP_{ij}^k$, where $j \in \{1,2\}$ is the probe index, and $$i = \begin{cases} 1 & \text{for matched probe,} \\ 0 & \text{for mismatch pobe,} \end{cases}$$

and $k \in \{1,2\}$ is the binding site. States within each category are numbered "left-to-right" with respect to location on the target.

The set of reversible reactions operating between unbound and bound states can be written as shown below, where the forward and backward reaction rates are indicated with $k_{i,j}$ and $k_{j,i}$, respectively. While the reaction rates themselves are difficult to compute, the ratios (affinity constants, $K_i^j = k_{i,j}/k_{j,i}$) may be computed from purely thermodynamic considerations, and are sufficient for the "equilibrium analysis."

$$T + P_{11} \underset{k_{2,1}}{\overset{k_{1,2}}{\rightleftharpoons}} TP_{11}^1 \quad T + P_{12} \underset{k_{8,1}}{\overset{k_{1,8}}{\rightleftharpoons}} TP_{12}^1$$

$$T + P_{01} \underset{k_{3,1}}{\overset{k_{1,3}}{\rightleftharpoons}} TP_{01}^1 \quad T + P_{02} \underset{k_{7,1}}{\overset{k_{1,7}}{\rightleftharpoons}} TP_{02}^1$$

$$T + P_{12} \underset{k_{4,1}}{\overset{k_{1,4}}{\rightleftharpoons}} TP_{12}^2 \quad T + P_{11} \underset{k_{8,1}}{\overset{k_{1,8}}{\rightleftharpoons}} TP_{11}^2$$

$$T + P_{02} \underset{k_{6,1}}{\overset{k_{1,6}}{\rightleftharpoons}} TP_{02}^2 \quad T + P_{01} \underset{k_{9,1}}{\overset{k_{1,9}}{\rightleftharpoons}} TP_{01}^2$$

To perform a stationary analysis, where these reactions are allowed to run to equilibrium, one begins by assuming that all complexes can be distinguished. In such case, the ODE's (ordinary differential equations) describing the dynamics of the system as follows.

Let $$\overline{X} = (X_1, X_2, X_3, X_4, X_5, X_6, X_7, X_8, X_9)^T$$
$$= ([T], [TP_{11}^1], [TP_{01}^1], [TP_{12}^2], [TP_{02}^2],$$
$$[TP_{12}^1], [TP_{02}^1], [TP_{11}^2], [TP_{01}^2])^T$$

Note that at equilibrium, $$\frac{d\overline{X}}{dt} = \overline{0}. \tag{1}$$

$$\frac{d[T]}{dt} = k_{2,1}[TP_{11}^1] + k_{3,1}[TP_{01}^1] + k_{4,1}[TP_{12}^2] + k_{5,1}[TP_{02}^2] +$$
$$k_{6,1}[TP_{12}^1] + k_{7,1}[TP_{02}^1] + k_{8,1}[TP_{11}^2] + k_{9,1}[TP_{01}^2] -$$
$$k_{1,2}[T][P_{11}] - k_{1,3}[T][P_{01}] - k_{1,4}[T][P_{12}] - k_{1,5}[T][P_{02}] -$$
$$k_{1,6}[T][P_{12}] - k_{1,7}[T][P_{02}] - k_{1,8}[T][P_{11}] - k_{1,9}[T][P_{01}]$$

$$\frac{d[TP_{11}^1]}{dt} = k_{1,2}[T][P_{11}] - k_{2,1}[TP_{11}^1] \tag{2}$$

$$\frac{d[TP_{01}^1]}{dt} = k_{1,3}[T][P_{01}] - k_{3,1}[TP_{01}^1] \tag{3}$$

$$\frac{d[TP_{12}^2]}{dt} = k_{1,4}[T][P_{12}] - k_{4,1}[TP_{12}^2] \tag{4}$$

$$\frac{d[TP_{02}^2]}{dt} = k_{1,5}[T][P_{02}] - k_{5,1}[TP_{02}^2] \tag{5}$$

$$\frac{d[TP_{12}^1]}{dt} = k_{1,6}[T][P_{12}] - k_{6,1}[TP_{12}^1] \tag{6}$$

$$\frac{d[TP_{02}^1]}{dt} = k_{1,7}[T][P_{02}] - k_{7,1}[TP_{02}^1] \tag{7}$$

$$\frac{d[TP_{11}^2]}{dt} = k_{1,8}[T][P_{11}] - k_{8,1}[TP_{11}^2] \tag{8}$$

$$\frac{d[TP_{01}^2]}{dt} = k_{1,9}[T][P_{01}] - k_{9,1}[TP_{01}^2] \tag{9}$$

Let $\qquad$ (10)

$$\overline{X} = (X_1, X_2, X_3, X_4, X_5, X_6, X_7, X_8, X_9)^T$$
$$= ([T], [TP_{11}^1], [TP_{01}^1], [TP_{12}^2], [TP_{02}^2],$$
$$[TP_{12}^1], [TP_{02}^1], [TP_{11}^2], [TP_{01}^2])^T$$

Note that at equilibrium, $$\frac{d\overline{X}}{dt} = \overline{0}. \tag{11}$$

Applying (11) to equations (2)-(9) yields $$k_{1,2}[T][P_{11}] = k_{2,1}[TP_{11}^1] \tag{12}$$
$$\Rightarrow K_1^2 \equiv \frac{k_{1,2}}{k_{2,1}} = \frac{[TP_{11}^1]}{[T][P_{11}]}$$

$$k_{1,3}[T][P_{01}] = k_{3,1}[TP_{01}^1] \tag{13}$$
$$\Rightarrow K_1^3 \equiv \frac{k_{1,3}}{k_{3,1}} = \frac{[TP_{01}^1]}{[T][P_{01}]}$$

-continued $$k_{1,4}[T][P_{12}] = k_{4,1}[TP_{12}^2] \tag{14}$$
$$\Rightarrow K_1^4 \equiv \frac{k_{1,4}}{k_{4,1}} = \frac{[TP_{12}^2]}{[T][P_{12}]}$$

$$k_{1,5}[T][P_{02}] = k_{5,1}[TP_{02}^2] \tag{15}$$
$$\Rightarrow K_1^5 \equiv \frac{k_{1,5}}{k_{5,1}} = \frac{[TP_{02}^2]}{[T][P_{02}]}$$

$$k_{1,6}[T][P_{12}] = k_{6,1}[TP_{12}^1] \tag{16}$$
$$\Rightarrow K_1^6 \equiv \frac{k_{1,6}}{k_{6,1}} = \frac{[TP_{12}^1]}{[T][P_{12}]}$$

$$k_{1,7}[T][P_{02}] = k_{7,1}[TP_{02}^1]$$
$$\Rightarrow K_1^7 \equiv \frac{k_{1,7}}{k_{7,1}} = \frac{[TP_{02}^1]}{[T][P_{02}]}$$

$$k_{1,8}[T][P_{11}] = k_{8,1}[TP_{11}^2]$$
$$\Rightarrow K_1^8 \equiv \frac{k_{1,8}}{k_{8,1}} = \frac{[TP_{11}^2]}{[T][P_{11}]}$$

$$k_{1,9}[T][P_{01}] = k_{9,1}[TP_{01}^2]$$
$$\Rightarrow K_1^9 \equiv \frac{k_{1,9}}{k_{9,1}} = \frac{[TP_{01}^2]}{[T][P_{01}]}$$

and applying it to equation (1) yields $$k_{2,1}[TP_{11}^1] + k_{3,1}[TP_{01}^1] + k_{4,1}[TP_{12}^2] + k_{5,1}[TP_{02}^2] + \tag{20}$$
$$k_{6,1}[TP_{12}^1] + k_{7,1}[TP_{02}^1] + k_{8,1}[TP_{11}^2] + k_{9,1}[TP_{01}^2] =$$
$$[T](k_{1,2}[P_{11}] + k_{1,3}[P_{01}] + k_{1,4}[P_{12}] + k_{1,5}[P_{02}] +$$
$$k_{1,6}[P_{12}] + k_{1,7}[P_{02}] + k_{1,8}[P_{11}] + k_{1,9}[P_{01}])$$

Equation (20) is a linear combination of (12), . . . , (19), and hence provides no additional information. Observe that $$\frac{d[T]}{dt} = -\frac{d}{dt}\{[TP_{11}^1] + [TP_{01}^1] + [TP_{12}^2] + [TP_{02}^2] +$$
$$[TP_{12}^1] + [TP_{02}^1] + [TP_{11}^2] + [TP_{01}^2]\}$$

or $$(1) = -\sum_{j=(2)}^{(9)} \{\text{equation } j\}$$

The constants $K_1^j$ for $j \in \{2, \ldots, 9\}$, appearing in equations (12)-(19), can be computed from probe sequence data. For each j, $$\Delta G_{total} = -RT \ln K_1^j,$$

where R is the gas constant and T is the temperature (in degrees Kelvin). Thus, we have $$K_1^j = \exp[-\Delta G_{total}/RT], \text{ where} \tag{21}$$

$$\Delta G_{total} = -\left(\frac{\Delta g_i}{\text{initiation}} + \frac{\Delta g_{symm}}{\text{symmetry}}\right) + \sum_T \frac{\Delta g_x}{\text{sequence data}}.$$

This notation and form follows the calculations set forth in Breslauer et al., supra; however, the calculation of $\Delta G$ has since been modified to follow the methods later-disclosed in SantaLucia, supra. Both versions of calculating $\Delta G$ are suitable for the model described herein.

The described model can be used to predict equilibrium concentrations of complexes $TP_{ij}\{i\in\{0,1\}, j\in\{1,2\}\}$, where $K_1^j$ can be calculated from the equation above (21), where $\Delta G_{total}$ is computed based on the sequence information. The following conservation rules must hold:

$$[P_{11}]_0 = [P_{11}] + [TP_{11}^1] + [TP_{11}^2] \tag{22}$$

$$[P_{01}]_0 = [P_{01}] + [TP_{01}^1] + [TP_{01}^2] \tag{23}$$

$$[P_{12}]_0 = [P_{12}] + [TP_{12}^1] + [TP_{12}^2] \tag{24}$$

$$[P_{02}]_0 = [P_{02}] + [TP_{02}^1] + [TP_{02}^2] \tag{25}$$

$$\begin{aligned}[T]_0 &= [T] + [TP_{11}^1] + [TP_{01}^1] + [TP_{12}^2] + [TP_{02}^2] + \\ &\quad [TP_{11}^2] + [TP_{01}^2] + [TP_{12}^1] + [TP_{02}^1] \\ &= [T] + ([P_{11}]_0 - [P_{11}]) + ([P_{01}]_0 - [P_{01}]) + \\ &\quad ([P_{12}]_0 - [P_{12}]) + ([P_{02}]_0 - [P_{02}])\end{aligned} \tag{26}$$

Note that in these expressions $[X]_0$ denotes initial concentration of X, which is a free parameter, and $[X]$ denotes its equilibrium concentration. Consider the system consisting of equations (12)(19) and the conservation rule equations (22)-(26). One has a system of 13 polynomial equations (some quadratic, others linear) in 13 unknowns: $X_1, \ldots, X_9$ (see (10)) and $[P_{11}], [P_{01}], [P_{12}], [P_{02}]$, with 5 free parameters: $[P_{11}]_0, [P_{01}]_0, [P_{12}]_0, [P_{02}]_0$, and $[T]_0$. Therefore, this algebraic system, when solved, yields the equilibrium concentrations. From these computed concentrations, we can evaluate the "match to-mismatch ratio" for each probe:

$$\left(\frac{[TP_{11}^1] + [TP_{11}^2]}{[TP_{01}^1] + [TP_{01}^2]}\right)_{full\ model} \text{ and } \left(\frac{[TP_{12}^2] + [TP_{12}^1]}{[TP_{02}^2] + [TP_{02}^1]}\right)_{full\ model}$$

In order to examine the effects of competition between probes $P_{11}$ and $P_{12}$ on the signals for each of them, one now compares this situation with the one where only $P_{11}$ and $P_{01}$ are present without $P_{12}$ or $P_{02}$, and vice versa. Hereinafter, the model introduced in this section as the Full Model and will compare its performance with the other two partial models, one consisting of $P_{11}, P_{01}$, and T only (referred to as Model I) and the other consisting of $P_{12}, P_{02}$, and T only (referred to as Model II).

Partial Model—Model I

This model consists of two probes $P_{11}, P_{01}$, and the target T only. One proceeds as before by solving the algebraic system of equations to evaluate:

$$\left(\frac{[TP_{11}^1] + [TP_{11}^2]}{[TP_{01}^1] + [TP_{01}^2]}\right)_I$$

Possible States:

Consider the following states:

(1) T (Target is unbound)

(2) $TP_{11}^1$; (3) $TP_{01}^1$ (Target is bound by "specific" hybridization.)

(8) $TP_{11}^2$; (9) $TP_{01}^2$ (Target is bound by "non-specific" hybridization)

Figure 3A:
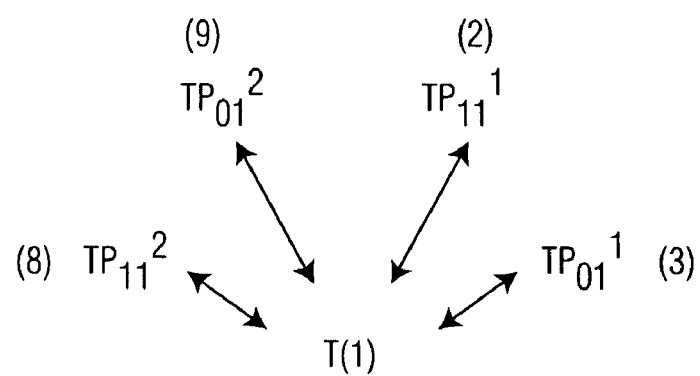
FIG. 3A shows a state transition diagram for the possible interactions of two PM/MM probe pairs and a target, T, under Model I, involving only states 1, 2, 3, 8, 9.

A state transition diagram for this partial model is depicted in FIG. 3A. A set of reversible reactions operating between unbound and bound states can be depicted as shown below.

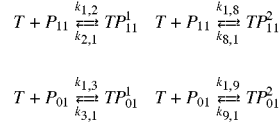

The following are the ordinary differential equations describing the dynamics of the system.

$$\begin{aligned}\frac{d[T]}{dt} &= k_{2,1}[TP_{11}^1] - k_{1,2}[T][P_{11}] + k_{3,1}[TP_{01}^1] - k_{1,3}[T][P_{01}] + \\ &\quad k_{8,1}[TP_{11}^2] - k_{1,8}[T][P_{11}] + k_{9,1}[TP_{01}^2] - k_{1,9}[T][P_{01}]\end{aligned} \tag{27}$$

$$\frac{d[TP_{11}^1]}{dt} = k_{1,2}[T][P_{11}] - k_{2,1}[TP_{11}^1] \tag{28}$$

$$\frac{d[TP_{01}^1]}{dt} = k_{1,3}[T][P_{01}] - k_{3,1}[TP_{01}^1] \tag{29}$$

$$\frac{d[TP_{11}^2]}{dt} = k_{1,8}[T][P_{11}] - k_{8,1}[TP_{11}^2] \tag{30}$$

$$\frac{d[TP_{01}^2]}{dt} = k_{1,9}[T][P_{01}] - k_{9,1}[TP_{01}^2] \tag{31}$$

Note that equations (28)-(31) are the same as equations (2), (3), (8), and (9) in the original full model system above, while equation (27) differs from (1), since it now involves only the states with probes $P_{11}$ and $P_{01}$.

At equilibrium, $d[.]/dt=0$ for all substances, i.e., T, $TP_{11}^1$, $TP_{11}^2$, $TP_{01}^1$, and $TP_{01}^2$, yielding:

$$K_1^2 = \frac{[TP_{11}^1]}{[T][P_{11}]} \tag{32}$$

$$K_1^3 = \frac{[TP_{01}^1]}{[T][P_{01}]} \tag{33}$$

$$K_1^8 = \frac{[TP_{11}^2]}{[T][P_{11}]} \tag{34}$$

$$K_1^9 = \frac{[TP_{01}^1]}{[T][P_{01}]} \tag{35}$$

Since nothing else has changed in the thermodynamics, $K_1^j$ computed from (21) are the same as before for $j\in\{2, 3, 8, 9\}$ and we have the following conservation rules:

$$[P_{11}]_0 = [P_{11}] + [TP_{11}^1] + [TP_{11}^2] \tag{36}$$

$$[P_{01}]_0 = [P_{01}] + [TP_{01}^1] + [TP_{01}^2] \tag{37}$$

$$[T]_0 = [T] + [TP_{11}^1] + [TP_{01}^1] + [TP_{11}^2] + [TP_{01}^2] \quad (38)$$
$$= [T] + ([P_{11}]_0 - [P_{11}]) + ([P_{01}]_0 - [P_{01}])$$

In this case one has
- 7 variables (unknowns): $[TP_{11}^1]$, $[TP_{11}^2]$, $[TP_{01}^1]$, $[TP_{01}^2]$, $[P_{11}]$, $[P_{01}]$, and $[T]$; and
- 7 polynomial equations: (32)-(35), (36), (37), and (38), with
- 3 free parameters $[P_{11}]_0$, $[P_{01}]_0$, and $[T]_0$.

Note that, for comparison with full model, the free parameters will need to be scaled to retain the same initial target-to-probe ratio.

Partial Model—Model II

This model consists of two probes $P_{12}$, $P_{02}$, and the target T only. One proceeds as before by solving the algebraic system of equations to evaluate:

$$\left( \frac{[TP_{12}^2] + [TP_{12}^1]}{[TP_{02}^2] + [TP_{02}^1]} \right)_{II}$$

And now considers the following states:

(1) T (Target is unbound.)

(4) $TP_{12}^2$; (5) $TP_{02}^2$ (Target is bound by "specific" hybridization)

(6) $TP_{12}^1$; (7) $TP_{02}^1$ (Target is bound by "non-specific" hybridization)

Figure 3B:
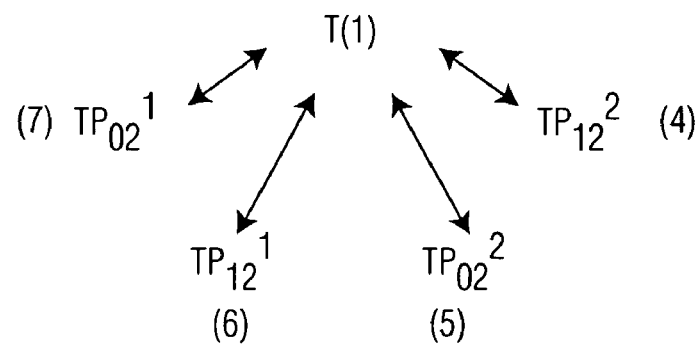
FIG. 3B shows a state transition diagram for the possible interactions of two PM/MM probe pairs and a target, T, under Model II, involving only states 1, 4, 5, 6, 7.

A state transition diagram is shown in FIG. 3B. The set of reversible reactions operating between unbound and bound states can be written as shown below.

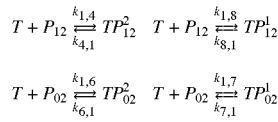

$$T + P_{12} \underset{k_{4,1}}{\overset{k_{1,4}}{\rightleftharpoons}} TP_{12}^2 \quad T + P_{12} \underset{k_{8,1}}{\overset{k_{1,8}}{\rightleftharpoons}} TP_{12}^1$$

$$T + P_{02} \underset{k_{6,1}}{\overset{k_{1,6}}{\rightleftharpoons}} TP_{02}^2 \quad T + P_{02} \underset{k_{7,1}}{\overset{k_{1,7}}{\rightleftharpoons}} TP_{02}^1$$

The following are the ordinary differential equations describing the dynamics of the system:

$$\frac{d[T]}{dt} = k_{4,1}[TP_{12}^2] - k_{1,4}[T][P_{12}] + k_{5,1}[TP_{02}^2] - k_{1,5}[T][P_{02}] + \quad (39)$$
$$k_{6,1}[TP_{12}^1] - k_{1,6}[T][P_{12}] + k_{7,1}[TP_{02}^1] - k_{1,7}[T][P_{02}]$$

$$\frac{d[TP_{12}^2]}{dt} = k_{1,4}[T][P_{12}] - k_{4,1}[TP_{12}^2] \quad (40)$$

$$\frac{d[TP_{02}^2]}{dt} = k_{1,5}[T][P_{02}] - k_{5,1}[TP_{02}^2] \quad (41)$$

$$\frac{d[TP_{12}^1]}{dt} = k_{1,6}[T][P_{12}] - k_{6,1}[TP_{12}^1] \quad (42)$$

$$\frac{d[TP_{02}^1]}{dt} = k_{1,7}[T][P_{02}] - k_{7,1}[TP_{02}^1] \quad (43)$$

$$\quad (44)$$

Note that equations (40)-(43) are the same as equations (4), (5), (6), and (7) in the original system above, while equation (39) differs from (1), since it now involves only the states with probes $P_{12}$ and $P_{02}$. At equilibrium, $d[.]/dt=0$ for all substances, i.e., T, $TP_{12}^2$, $TP_{12}^1$, $TP_{02}^2$, and $TP_{02}^1$, yielding:

$$K_1^4 = \frac{[TP_{12}^2]}{[T][P_{12}]} \quad (45)$$

$$K_1^5 = \frac{[TP_{02}^2]}{[T][P_{02}]} \quad (46)$$

$$K_1^6 = \frac{[TP_{12}^1]}{[T][P_{12}]} \quad (47)$$

$$K_1^7 = \frac{[TP_{02}^1]}{[T][P_{02}]} \quad (48)$$

Again, since nothing else has changed in the thermodynamics, $K_1^j$ computed from (21) are the same as before for $j \in \{4, 5, 6, 7\}$, and we have the following conservation rules:

$$[P_{12}]_0 = [P_{12}] + [TP_{12}^2] + [TP_{12}^1] \quad (49)$$

$$[P_{02}]_0 = [P_{02}] + [TP_{02}^2] + [TP_{02}^1] \quad (50)$$

$$[T]_0 = [T] + [TP_{12}^2] + [TP_{02}^2] + [TP_{12}^1] + [TP_{02}^1] \quad (51)$$
$$= [T] + ([P_{12}]_0 - [P_{12}]) + ([P_{02}]_0 - [P_{02}])$$

In this case, one also has:

7 variables: $[TP_{12}^2]$, $[TP_{12}^1]$, $[TP_{02}^2]$, $[TP_{02}^1]$, $[P_{12}]$, $[P_{02}]$, and $[T]$; and 7 equations: (45)-(48), (49), (50), and (51), with 3 free parameters $[P_{12}]_0$, $[P_{02}]_0$, and $[T]_0$.

As above, the parameters will need to be scaled. In practice, once the exact nucleotide sequences of T, $P_{11}$, $P_{01}$, $P_{12}$, and $P_{02}$ are determined from the needs of the biological assay, one can compute $K_1^j$ explicitly, and then solve for the unknowns in all three setups: Full Model, Model I, and Model II. With these computed ratio values, one is ready to evaluate and compare the models in order to discern the effects of competition:

$$\left(\frac{P_{11}}{P_{01}}\right)_{full} \text{ vs. } \left(\frac{P_{11}}{P_{01}}\right)_I \text{ and}$$

$$\left(\frac{P_{12}}{P_{02}}\right)_{full} \text{ vs. } \left(\frac{P_{12}}{P_{02}}\right)_{II}$$

Full Model

In order to simplify the algebraic system of equation, one can rename the unknown variables as follows:

$$X_1 = [T]$$

$$X_2 = [TP_{11}^1] \quad X_6 = [TP_{12}^1] \quad Y_1 = [P_{11}]$$

$$X_3 = [TP_{01}^1] \quad X_7 = [TP_{02}^1] \quad Y_2 = [P_{01}]$$

$$X_4 = [TP_{12}^2] \quad X_8 = [TP_{11}^2] \quad Y_3 = [P_{12}]$$

-continued
$$X_5 = [TP_{02}^2] \quad X_9 = [TP_{01}^2] \quad Y_4 = [P_{02}]$$

The constant parameters in the system are initially left in their symbolic form.

$$K_1^2; K_1^3; K_1^4; K_1^5; K_1^6; K_1^7; K_1^8; K_1^9;$$
$$a_0 = [P_{11}]_0; \quad b_0 = [P_{01}]_0;$$
$$c_0 = [P_{12}]_0; \quad d_0 = [P_{02}]_0;$$
$$e_0 = [T]_0.$$

Equations (12)-(19) and (22)-(26) can now be rewritten in terms of $\{X_i; Y_j\}$ as follows.

$$\left.\begin{aligned}
[TP_{11}^1] &= K_1^2[T][P_{11}] \Rightarrow & X_2 &= K_1^2 X_1 Y_1 \\
[TP_{01}^1] &= K_1^3[T][P_{01}] \Rightarrow & X_3 &= K_1^3 X_1 Y_2 \\
[TP_{12}^2] &= K_1^4[T][P_{12}] \Rightarrow & X_4 &= K_1^4 X_1 Y_3 \\
[TP_{02}^2] &= K_1^5[T][P_{02}] \Rightarrow & X_5 &= K_1^5 X_1 Y_4 \\
[TP_{12}^1] &= K_1^6[T][P_{12}] \Rightarrow & X_6 &= K_1^6 X_1 Y_3 \\
[TP_{02}^1] &= K_1^7[T][P_{02}] \Rightarrow & X_7 &= K_1^7 X_1 Y_4 \\
[TP_{11}^2] &= K_1^8[T][P_{11}] \Rightarrow & X_8 &= K_1^8 X_1 Y_1 \\
[TP_{01}^2] &= K_1^9[T][P_{01}] \Rightarrow & X_9 &= K_1^9 X_1 Y_2 \\
[P_{11}]_0 &= [P_{11}] + [TP_{11}^1] + [TP_{11}^2] \Rightarrow & a_0 &= X_2 + X_8 + Y_1 \\
[P_{01}]_0 &= [P_{01}] + [TP_{01}^1] + [TP_{01}^2] \Rightarrow & b_0 &= X_3 + X_9 + Y_2 \\
[P_{12}]_0 &= [P_{12}] + [TP_{12}^1] + [TP_{12}^2] \Rightarrow & c_0 &= X_4 + X_6 + Y_3 \\
[P_{02}]_0 &= [P_{02}] + [TP_{02}^1] + [TP_{02}^2] \Rightarrow & d_0 &= X_5 + X_7 + Y_4 \\
[T]_0 &= [T] + [TP_{11}^1] + [TP_{01}^1] + & e_0 &= X_1 + X_2 + X_3 + \\
[TP_{12}^2] &+ [TP_{02}^2] + [TP_{11}^2] + & & X_4 + X_5 + X_6 + \\
[TP_{01}^2] &+ [TP_{12}^1] + [TP_{02}^1] \Rightarrow & & X_7 + X_8 + X_9
\end{aligned}\right\} \quad (52)$$

Model I

Now, we consider a system of algebraic equations representing the concentrations at equilibrium and involving unknown variables $X_1, X_2, X_3, X_8, X_9, Y_1,$ and $Y_2$, and constant parameters $K_1^2, K_1^3, K_1^8, K_1^9, a_0, b_0,$ and $e_0$. Thus, in a manner analogous to that derived for the full model in the previous section, one may rewrite the equations (32), (33), (34), (35), (36), (37), and (38) in terms of $\{X_i; Y_j\}$, as shown below.

$$\left.\begin{aligned}
X_2 &= K_1^2 X_1 Y_1 \\
X_3 &= K_1^3 X_1 Y_2 \\
X_8 &= K_1^8 X_1 Y_1 \\
X_9 &= K_1^9 X_1 Y_2 \\
a_0 &= [P_{11}]_0 = X_2 + X_8 + Y_1 \\
b_0 &= [P_{01}]_0 = X_3 + X_9 + Y_2 \\
e_0 &= [T]_0 = X_1 + X_2 + X_3 + X_8 + X_9
\end{aligned}\right\} \quad (53)$$

Model II

Next, consider a system of algebraic equations representing the concentrations at equilibrium and involving unknown variables $X_1, X_4, X_5, X_6, X_7, Y_3,$ and $Y_4$, and constant parameters $K_1^4, K_1^5, K_1^6, K_1^7, c_0, d_0,$ and $e_0$. Once again one may rewrite the equations (45), (46), (47), (48), (49), (50), and (51) in terms of $\{X_i; Y_j\}$, as shown below.

$$\left.\begin{aligned}
X_4 &= K_1^4 X_1 Y_3 \\
X_5 &= K_1^5 X_1 Y_4 \\
X_6 &= K_1^6 X_1 Y_3 \\
X_7 &= K_1^7 X_1 Y_4 \\
c_0 &= [P_{12}]_0 = X_4 + X_6 + Y_3 \\
d_0 &= [P_{02}]_0 = X_5 + X_7 + Y_4 \\
e_0 &= [T]_0 = X_1 + X_4 + X_5 + X_6 + X_7
\end{aligned}\right\} \quad (54)$$

Note that with the exception of the conservation rules for $[T]$ (i.e., the last equations in (52), (53), and (54)) under the different models, one has $(52)=(53)\cup(54)$.

System Reduction—Model I

Starting with (53), one may obtain the following linear equalities:

$$Y_1 = a_0 - X_2 - X_8 \quad (55)$$

$$Y_2 = b_0 - X_3 - X_9 \quad (56)$$

Furthermore, since $$\frac{X_2}{X_8} = \frac{K_1^2 X_1 Y_1}{K_1^8 X_1 Y_1} = \frac{K_1^2}{K_1^8} \Longrightarrow X_8 = \frac{K_1^8}{K_1^2} X_2 \quad (57)$$

$$\frac{X_3}{X_9} = \frac{K_1^3 X_1 Y_2}{K_1^9 X_1 Y_2} = \frac{K_1^3}{K_1^9} \Longrightarrow X_9 = \frac{K_1^9}{K_1^3} X_3 \quad (58)$$

one may simplify to obtain:

$$\begin{aligned}
X_2 &= K_1^2 X_1 Y_1 = K_1^2 X_1 (a_0 - X_2 - X_8) \\
&= K_1^2 X_1 \left(a_0 - X_2 - \frac{K_1^8}{K_1^2} X_2\right) \\
&= K_1^2 X_1 \left(a_0 - X_2 \left[1 + \frac{K_1^8}{K_1^2}\right]\right) \\
&= K_1^2 X_1 a_0 - K_1^2 X_1 X_2 \left[1 + \frac{K_1^8}{K_1^2}\right] \\
&= K_1^2 X_1 a_0 - X_1 X_2 [K_1^2 + K_1^8] \\
X_2 + X_1 X_2 [K_1^2 + K_1^8] &= a_0 K_1^2 X_1 \\
\therefore \boxed{X_2 = \frac{a_0 K_1^2 X_1}{1 + X_1 (K_1^2 + K_1^8)}}
\end{aligned} \quad (59)$$

and

-continued $$X_3 = K_1^9 X_1 Y_2 = K_1^3 X_1 (b_0 - X_3 - X_9) \quad (60)$$

$$= K_1^9 X_1 \left( b_0 - X_3 - \frac{K_1^9}{K_1^3} X_3 \right)$$

$$= K_1^9 X_1 \left( b_0 - X_3 \left[ 1 + \frac{K_1^9}{K_1^3} \right] \right)$$

$$= K_1^9 X_1 b_0 - K_1^3 X_1 X_3 \left[ 1 + \frac{K_1^9}{K_1^3} \right]$$

$$= K_1^9 X_1 b_0 - X_1 X_3 [K_1^3 + K_1^9]$$

$$X_3 + X_1 X_3 [K_1^3 + K_1^9] = b_0 K_1^9 X_1$$

$$\therefore \boxed{X_3 = \frac{b_0 K_1^9 X_1}{1 + X_1 (K_1^3 + K_1^9)}}$$

We also obtain, from (57), $$X_8 = \frac{K_1^8}{K_1^2} X_2 = \frac{K_1^8}{K_1^2} \frac{a_0 K_1^2 X_1}{1 + X_1 (K_1^2 + K_1^8)} \quad (61)$$

$$= \boxed{\frac{a_0 K_1^8 X_1}{1 + X_1 (K_1^2 + K_1^8)} = X_8}$$

and from (58):

$$X_9 = \frac{K_1^9}{K_1^3} X_3 = \frac{K_1^9}{K_1^3} \frac{b_0 K_1^3 X_1}{1 + X_1 (K_1^3 + K_1^9)} \quad (62)$$

$$= \boxed{\frac{b_0 K_1^9 X_1}{1 + X_1 (K_1^3 + K_1^9)} = X_9}$$

Finally, equations (59), (60), (61), and (62) can be solved to express $X_2$, $X_3$, $X_8$, and $X_9$, respectively, in terms of $X_1$. Now, from (55), (57), and (59), one derives:

$$Y_1 = a_0 - X_2 - X_8 = a_0 - X_2 \left( 1 + \frac{K_1^8}{K_1^2} \right) \quad (63)$$

$$= a_0 - \frac{a_0 K_1^2 X_1}{1 + X_1 (K_1^2 + K_1^8)} \left( 1 + \frac{K_1^8}{K_1^2} \right)$$

$$= a_0 - \frac{a_0 X_1 (K_1^2 + K_1^8)}{1 + X_1 (K_1^2 + K_1^8)}$$

$$= a_0 \left[ \frac{1 + X_1 (K_1^2 + K_1^8) - X_1 (K_1^2 + K_1^8)}{1 + X_1 (K_1^2 + K_1^8)} \right]$$

$$= \frac{a_0}{1 + X_1 (K_1^2 + K_1^8)}$$

$$\therefore \boxed{Y_1 = \frac{a_0}{1 + X_1 (K_1^2 + K_1^8)}}$$

Similarly, one derives:

$$Y_2 = b_0 - X_3 - X_9 = b_0 - X_3 \left( 1 + \frac{K_1^9}{K_1^3} \right) \quad (64)$$

-continued $$= b_0 - \frac{b_0 K_1^3 X_1}{1 + X_1 (K_1^3 + K_1^9)} \left( 1 + \frac{K_1^9}{K_1^3} \right)$$

$$= b_0 - \frac{b_0 X_1 (K_1^3 + K_1^9)}{1 + X_1 (K_1^3 + K_1^9)}$$

$$= b_0 \left[ \frac{1 + X_1 (K_1^3 + K_1^9) - X_1 (K_1^3 + K_1^9)}{1 + X_1 (K_1^3 + K_1^9)} \right]$$

$$= \frac{b_0}{1 + X_1 (K_1^3 + K_1^9)}$$

$$\therefore \boxed{Y_2 = \frac{b_0}{1 + X_1 (K_1^3 + K_1^9)}}$$

A final simplification yields a univariate rational function only in $X_1$ equating to a constant $e_0$:

$$e_0 = X_1 + X_2 + X_3 + X_8 + X_9 \quad \text{(by (53))} \quad (65)$$

$$= X_1 + X_1 \frac{a_0 K_1^2}{1 + X_1 (K_1^2 + K_1^8)} +$$

$$X_1 \frac{b_0 K_1^3}{1 + X_1 (K_1^3 + K_1^9)} \quad \text{(by (59); (60))} +$$

$$X_1 \frac{a_0 K_1^8}{1 + X_1 (K_1^2 + K_1^8)} +$$

$$X_1 \frac{b_0 K_1^9}{1 + X_1 (K_1^3 + K_1^9)} \quad \text{(by (61); (62))}$$

$$e_0 = X_1 \left[ 1 + a_0 \frac{K_1^2 + K_1^8}{1 + X_1 (K_1^2 + K_1^8)} + b_0 \frac{K_1^3 + K_1^9}{1 + X_1 (K_1^3 + K_1^9)} \right]$$

Since the terms $(K_1^2 + K_1^8)$ and $(K_1^3 + K_1^9)$ appear frequently, in order to express the preceding equations in a simpler form, introduced is a short-hand notation shown below. Let $$s_{28} \equiv K_1^2 + K_1^8; \quad s_{39} \equiv K_1^3 + K_1^9; \quad \text{and } x \equiv X_1.$$

In simplified form, the equation (65) becomes:

$$x \left( 1 + a_0 \frac{s_{28}}{1 + s_{28} x} + b_0 \frac{s_{39}}{1 + s_{39} x} \right) = e_0 \quad (66)$$

$$x \left( \frac{((1 + s_{28} x)(1 + s_{39} x) + a_0 s_{28}(1 + s_{39} x) + b_0 s_{39}(1 + s_{28} x))}{((1 + s_{28} x)(1 + s_{39} x))} \right) = e_0$$

$$x((1 + s_{28} x)(1 + s_{39} x) + a_0 s_{28}(1 + s_{39} x) + b_0 s_{39}(1 + s_{28} x)) =$$

$$e_0 (1 + s_{28} x)(1 + s_{39} x);$$

$$(s_{28} s_{39}) x^3 + (s_{28} + s_{39} + s_{28} s_{39} [a_0 + b_0 - e_0]) x^2 + 1 +$$

$$s_{28}[a_0 - e_0] + s_{39}[b_0 - e_0]) x - e_0 = 0$$

Now the cubic polynomial equation (66) must be solved for the unknown $\chi = X_1$, and then the solution can be substituted into (59)-(64) in order to solve for the rest of the variables. One may obtain the solutions in their symbolic form using MATHEMATICA computer algebra system (see Wolfram, S. *The Mathematica Book.* Cambridge University Press, 4th edition, (1999)), as the three possible roots may be easily expressed in radicals. More to the point, one only needs to solve for $$\left(\frac{P_{11}}{P_{01}}\right)_I = \left[\frac{[TP_{11}^1] + [TP_{11}^2]}{[TP_{01}^1] + [TP_{01}^2]}\right]_I \quad (67)$$

$$= \frac{X_2 + X_8}{X_3 + X_9}$$

$$= \left(\frac{a_0 K_1^2 x}{1 + s_{28} x} + \frac{a_0 K_1^8 x}{1 + s_{28} x}\right) / \left(\frac{b_0 K_1^3 x}{1 + s_{39} x} + \frac{b_0 K_1^9 x}{1 + s_{39} x}\right)$$

or $$\left(\frac{P_{11}}{P_{01}}\right)_I = \left(\frac{a_0 s_{28} x}{1 + s_{28} x}\right) / \left(\frac{b_0 s_{39} x}{1 + s_{39} x}\right)$$

$$= \boxed{\frac{a_0}{b_0} \frac{s_{28}}{s_{39}} \frac{1 + s_{39} x}{1 + s_{28} x}}$$

$$= \frac{a_0}{b_0} \frac{s_{28}}{s_{39}} \frac{s_{39} + 1/x}{s_{28} + 1/x}$$

where $\chi$ is at solution of (66).

System Reduction—Model II

As before, starting with (54), one obtains the following linear equalities:

$$Y_3 = c_0 - X_4 - X_6 \quad (68)$$

$$Y_4 = d_0 - X_5 - X_7 \quad (69)$$

Since $$\frac{X_4}{X_6} = \frac{K_1^4 X_1 Y_3}{K_1^6 X_1 Y_3} = \frac{K_1^4}{K_1^6} \Longrightarrow X_6 = \frac{K_1^6}{K_1^4} X_4 \quad (70)$$

$$\frac{X_5}{X_7} = \frac{K_1^6 X_1 Y_4}{K_1^7 X_1 Y_4} = \frac{K_1^5}{K_1^7} \Longrightarrow X_7 = \frac{K_1^7}{K_1^5} X_5 \quad (71)$$

we obtain $$X_4 = K_1^4 X_1 Y_3 = K_1^4 X_1 \left(c_0 - X_4 \left[1 + \frac{K_1^6}{K_1^4}\right]\right) \quad (72)$$

$$= K_1^4 X_1 c_0 - X_1 X_4 (K_1^4 + K_1^6)$$

$$\therefore \boxed{X_4 = \frac{c_0 K_1^4 X_1}{1 + X_1(K_1^4 + K_1^6)}}$$

and $$X_5 = K_1^5 X_1 Y_4 \quad (73)$$

$$= K_1^5 X_1 \left(d_0 - X_5 \left[1 + \frac{K_1^7}{K_1^5}\right]\right)$$

$$= K_1^5 X_1 d_0 - X_1 X_5 (K_1^5 + K_1^7)$$

$$\therefore \boxed{X_5 = \frac{d_0 K_1^5 X_1}{1 + X_1(K_1^5 + K_1^7)}}$$

Furthermore, from (70) and (72), we obtain $$X_6 = \frac{K_1^6}{K_1^4} X_4 \quad (74)$$

-continued $$= \frac{K_1^6}{K_1^4} \frac{c_0 K_1^4 X_1}{1 + X_1(K_1^4 + K_1^6)}$$

$$= \boxed{\frac{c_0 K_1^6 X_1}{1 + X_1(K_1^4 + K_1^6)} = X_6}$$

and from (71) and (73), $$X_7 = \frac{K_1^7}{K_1^5} X_5 \quad (75)$$

$$= \frac{K_1^7}{K_1^5} \frac{d_0 K_1^6 X_1}{1 + X_1(K_1^6 + K_1^7)}$$

$$= \boxed{\frac{d_0 K_1^7 X_1}{1 + X_1(K_1^6 + K_1^7)} = X_7}$$

Finally, equations (72) (73), (74), and (75) can be solved to express $X_4$, $X_5$, $X_6$, and $X_7$, respectively, in terms of $X_1$.

From (68), (70), and (72), we derive $$Y_3 = c_0 - X_4 - X_6 \quad (76)$$

$$= c_0 - X_4 \left(1 + \frac{K_1^6}{K_1^4}\right)$$

$$= c_0 - \frac{c_0 K_1^4 X_1}{1 + X_1(K_1^4 + K_1^6)} \left(1 + \frac{K_1^6}{K_1^4}\right)$$

$$= c_0 - \frac{c_0 X_1 (K_1^4 + K_1^6)}{1 + X_1(K_1^4 + K_1^6)}$$

$$= c_0 \left[\frac{1 + X_1(K_1^4 + K_1^6) - X_1(K_1^4 + K_1^6)}{1 + X_1(K_1^4 + K_1^6)}\right]$$

$$= \frac{c_0}{1 + X_1(K_1^4 + K_1^6)}$$

$$\therefore \boxed{Y_3 = \frac{c_0}{1 + X_1(K_1^4 + K_1^6)}}$$

Similarly, we derive $$Y_4 = d_0 - X_5 - X_7 \quad (77)$$

$$= d_0 - X_5 \left(1 + \frac{K_1^7}{K_1^5}\right)$$

$$= d_0 - \frac{d_0 K_1^5 X_1}{1 + X_1(K_1^5 + K_1^7)} \left(1 + \frac{K_1^7}{K_1^5}\right)$$

$$= d_0 - \frac{d_0 X_1 (K_1^5 + K_1^7)}{1 + X_1(K_1^5 + K_1^7)}$$

$$= d_0 \left[\frac{1 + X_1(K_1^5 + K_1^7) - X_1(K_1^5 + K_1^7)}{1 + X_1(K_1^5 + K_1^7)}\right]$$

$$= \frac{d_0}{1 + X_1(K_1^5 + K_1^7)}$$

$$\therefore \boxed{Y_4 = \frac{d_0}{1 + X_1(K_1^5 + K_1^7)}}$$

Putting it all together, we derive the univariate rational equation for $X_1$.

or $$e_0 = X_1 + X_4 + X_5 + X_6 + X_7 \quad \text{(by (54))} \tag{78}$$

$$= X_1 + X_1 \frac{c_0 K_1^4}{1 + X_1(K_1^4 + K_1^6)} +$$

$$X_1 \frac{d_0 K_1^5}{1 + X_1(K_1^5 + K_1^7)} \quad \text{(by (72), (73))} +$$

$$X_1 \frac{c_0 K_1^6}{1 + X_1(K_1^4 + K_1^6)} +$$

$$X_1 \frac{d_0 K_1^7}{1 + X_1(K_1^5 + K_1^7)} \quad \text{(by (74), (75))}$$

$$e_0 = X_1 \left[ 1 + c_0 \frac{K_1^4 + K_1^6}{1 + X_1(K_1^4 + K_1^6)} + d_0 \frac{K_1^5 + K_1^7}{1 + X_1(K_1^5 + K_1^7)} \right]$$

As before, we abbreviate the terms $(K_1^4 + K_1^6)$ and $(K_1^5 + K_1^7)$ by short-hand notation, shown below. Let $$s_{46} \equiv K_1^4 + K_1^6; \; s_{57} \equiv K_1^5 + K_1^7; \text{ and } y \equiv X_1.$$

Note that, in order to avoid confusion a different abbreviation for $X_i$ (i.e., y), was introduced intentionally since the equation to be solved in this case differs from equation (66). Then (78) can be expressed as:

$$y\left(1 + c_0 \frac{s_{46}}{1 + s_{46}y} + d_0 \frac{s_{57}}{1 + s_{57}y}\right) = e_0 \tag{79}$$

$$y\left(\frac{(1+s_{46}y)(1+s_{57}y) + c_0 s_{46}(1+s_{57}y) + d_0 s_{57}(1+s_{46}y)}{(1+s_{46}y)(1+s_{57}y)}\right) = e_0$$

$$y((1+s_{46}y)(1+s_{57}y) + c_0 s_{46}(1+s_{57}y) + d_0 s_{57}(1+s_{46}y)) =$$

$$e_0(1+s_{46}y)(1+s_{57}y);$$

or $$(s_{46}s_{57})y^3 + (s_{46} + s_{57} + s_{46}s_{57}[c_0 + d_0 - e_0])y^2 +$$

$$(1 + s_{46}[c_0 - e_0] + s_{57}[d_0 - e_0])y - e_0 = 0$$

Again, the cubic polynomial equation (79) must be solved for $y=X_1$, and then the solution can be substituted into (72)-(77) for the rest of the variables. Actually, one only needs $$\left(\frac{P_{12}}{P_{02}}\right)_{11} = \left[\frac{[TP_{12}^2] + [TP_{12}^1]}{[TP_{02}^2] + [TP_{02}^1]}\right]_{11} \tag{80}$$

$$= \frac{X_4 + X_6}{X_5 + X_7}$$

$$= \left(\frac{c_0 K_1^4 y}{1 + s_{46}y} + \frac{c_0 K_1^6 y}{1 + s_{46}y}\right) \bigg/ \left(\frac{d_0 K_1^5 y}{1 + s_{57}y} + \frac{d_0 K_1^7 y}{1 + s_{57}y}\right)$$

or $$\left(\frac{P_{12}}{P_{02}}\right)_{11} = \left(\frac{c_0 s_{46} y}{1 + s_{46}y}\right) \bigg/ \left(\frac{d_0 s_{57} y}{1 + s_{57}y}\right)$$

$$= \frac{c_0}{d_0} \frac{s_{46}}{s_{57}} \frac{1 + s_{57}y}{1 + s_{46}y}$$

$$= \frac{c_0}{d_0} \frac{s_{46}}{s_{57}} \frac{s_{57} + 1/y}{s_{46} + 1/y}$$

where y solves (79).

System Reduction—Full Model

As noted above, the system (52) of equations for the Full Model is simply the union of the systems (53) and (54) for models I and II, respectively, with the exception of the conservation rule for [T], i.e., the equation for $X_1$. Therefore, while the equation for $X_1$ itself must be handled separately, the derivations from sections Model I and Model II above can be duplicated to obtain equations for all the variables in terms of $X_1$. For convenience, one gathers the resulting equations in one place, as shown below.

$$X_2 = \frac{a_0 K_1^2 X_1}{1 + X_1(K_1^2 + K_1^8)} \quad \text{(see (59))} \tag{81}$$

$$X_3 = \frac{b_0 K_1^3 X_1}{1 + X_1(K_1^3 + K_1^9)} \quad \text{(see (60))} \tag{82}$$

$$X_4 = \frac{c_0 K_1^4 X_1}{1 + X_1(K_1^4 + K_1^6)} \quad \text{(see (72))} \tag{83}$$

$$X_5 = \frac{d_0 K_1^5 X_1}{1 + X_1(K_1^5 + K_1^7)} \quad \text{(see (73))} \tag{84}$$

$$X_6 = \frac{c_0 K_1^6 X_1}{1 + X_1(K_1^4 + K_1^6)} \quad \text{(see (74))} \tag{85}$$

$$X_7 = \frac{d_0 K_1^7 X_1}{1 + X_1(K_1^5 + K_1^7)} \quad \text{(see (75))} \tag{86}$$

$$X_8 = \frac{a_0 K_1^8 X_1}{1 + X_1(K_1^2 + K_1^8)} \quad \text{(see (61))} \tag{87}$$

$$X_9 = \frac{b_0 K_1^9 X_1}{1 + X_1(K_1^3 + K_1^9)} \quad \text{(see (62))} \tag{88}$$

$$Y_1 = \frac{a_0}{1 + X_1(K_1^2 + K_1^8)} \quad \text{(see (63))} \tag{89}$$

$$Y_2 = \frac{b_0}{1 + X_1(K_1^3 + K_1^9)} \quad \text{(see (64))} \tag{90}$$

$$Y_3 = \frac{c_0}{1 + X_1(K_1^4 + K_1^6)} \quad \text{(see (76))} \tag{91}$$

$$Y_4 = \frac{d_0}{1 + X_1(K_1^5 + K_1^7)} \quad \text{(see (77))} \tag{92}$$

It remains to derive the univariate equation in $X_1$. Since the terms $(K_1^2 + K_1^8)$, $(K_1^3 + K_1^9)$, $(K_1^4 + K_1^6)$, and $(K_1^5 + K_1^7)$ appear frequently in the following derivation, as in the previous sections, we abbreviate these terms with the short-hand notation given below. As in discussions of Models I and II above, let $$s_{28} \equiv K_1^2 + K_1^8; \quad s_{39} \equiv K_1^3 + K_1^9;$$
$$s_{46} \equiv K_1^4 + K_1^6; \quad s_{57} \equiv K_1^5 + K_1^7;$$

and let $z \equiv X_1$.

Note again that a different symbol for $X_1$ has to be employed to avoid confusion with equations (66) and (79).

$$e_0 = X_1 + X_2 + X_3 + X_4 + X_5 + X_6 + X_7 + X_8 + X_9 \text{ (by (52))} \quad (93)$$
$$= z + z \frac{a_0 K_1^2}{1 + s_{28}z} + z \frac{b_0 K_1^3}{1 + s_{39}z} + z \frac{c_0 K_1^4}{1 + s_{46}z} +$$
$$z \frac{d_0 K_1^5}{1 + s_{57}z} \text{ (by (81) – (84))} +$$
$$z \frac{c_0 K_1^6}{1 + s_{46}z} + z \frac{d_0 K_1^7}{1 + s_{57}z} + z \frac{a_0 K_1^8}{1 + zs_{28}} + z \frac{b_0 K_1^9}{1 + zs_{39}} \text{ (by (85) – (88))}$$
$$= z \left[ 1 + a_0 \frac{K_1^2 + K_1^8}{1 + s_{28}z} + b_0 \frac{K_1^3 + K_1^9}{1 + s_{39}z} + c_0 \frac{K_1^4 + K_1^6}{1 + s_{46}z} + d_0 \frac{K_1^5 + K_1^7}{1 + s_{57}z} \right]$$

or $$e_0 = z \left[ 1 + \frac{a_0 s_{28}}{1 + s_{28}z} + \frac{b_0 s_{39}}{1 + s_{39}z} + \frac{c_0 s_{46}}{1 + s_{46}z} + \frac{d_0 s_{57}}{1 + s_{57}z} \right] \quad (94)$$

or $$\frac{(1+s_{28}z)(1+s_{39}z)}{(1+s_{46}z)(1+s_{57}z)} e_0 = z[(1+s_{28}z)(1+s_{39}z)(1+s_{46}z) \quad (95)$$
$$(1+s_{57}z) + a_0 s_{28}(1+s_{39}z)(1+s_{46}z)$$
$$(1+s_{57}z) + b_0 s_{39}(1+s_{28}z)(1+s_{46}z)$$
$$(1+s_{57}z) + c_0 s_{46}(1+s_{28}z)(1+s_{39}z)$$
$$(1+s_{57}z) + d_0 s_{57}(1+s_{28}z)(1+s_{39}z)$$
$$(1+s_{46}z)]$$

Since one now has a $5_{th}$ order polynomial equation in z to solve, and since its roots cannot be expressed symbolically in a closed form, one must resort to a purely numerical approach. Nonetheless, the match-to-mismatch ratio signals can be obtained in terms of z.

$$\left(\frac{P_{11}}{P_{01}}\right)_{full} = \left[\frac{[TP_{11}^1] + [TP_{01}^2]}{[TP_{01}^1] + [TP_{01}^2]}\right]_{full} \quad (96)$$
$$= \frac{X_2 + X_8}{X_3 + X_9}$$
$$= \boxed{\frac{a_0}{b_0} \frac{s_{28}}{s_{39}} \frac{1 + s_{39}z}{1 + s_{28}z}}$$
$$= \frac{a_0}{b_0} \frac{s_{28}}{s_{39}} \frac{s_{39} + 1/z}{s_{28} + 1/z} \text{ (see ((67))}$$

and $$\left(\frac{P_{12}}{P_{02}}\right)_{full} = \left[\frac{[TP_{12}^2] + [TP_{12}^1]}{[TP_{02}^2] + [TP_{02}^1]}\right]_{full} \quad (97)$$
$$= \frac{X_4 + X_6}{X_5 + X_7}$$
$$= \boxed{\frac{c_0}{d_0} \frac{s_{46}}{s_{57}} \frac{1 + s_{57}z}{1 + s_{46}z}}$$
$$= \frac{c_0}{d_0} \frac{s_{46}}{s_{57}} \frac{s_{57} + 1/z}{s_{46} + 1/z} \text{ (see (80)),}$$

where z solves (95).

Normalized Discrimination: Δ-Plot

Figure 4:
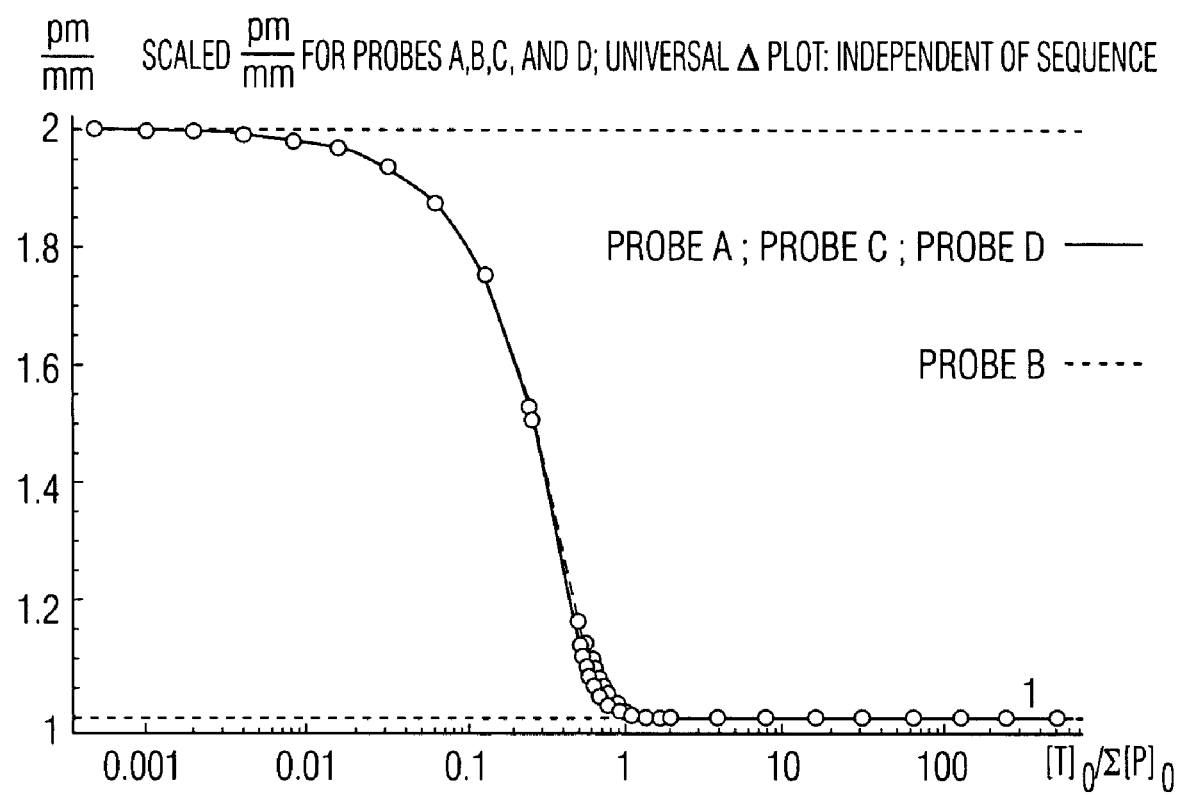
FIG. 4 is the "Δ plot," i.e., a universal representation of the discrimination of signal achieved with each of four different probe pairs each having different sequences, which separately form hybridization complexes with a target, as a function of the ratio of the initial concentrations of target and probes.

To display the results of the computation and to describe the principal effects of competitive hybridization in a graphical manner, a "normalized discrimination" plot is provided, also referred to herein as a Δ-plot. This plot displays, in a manner that is independent of the specific sequences of a PM/MM probe pair, the normalized discrimination, herein denoted by Δ, and denoted in FIG. 4 by the ratio "pm/mm", as a function of the molar ratio, $[T]_0/\Sigma[P]_0$ of the initial target concentration and the sum of initial probe concentrations. Here, the normalized discrimination represents the ratio of the amounts of probe-target complexes formed by PM and MM probes, normalized by the respective sequence-specific affinities. To the extent that affinities, calculated by summing over sequence-specific NN interactions on the entire region of the interactions, stabilize a duplex, the shape of the normalized discrimination plot is independent of the specific probe sequences under consideration. This makes the Δ-plot a valuable tool for the determination of the effect of competition wherein competitive hybridization manifests itself in the form of a shift of the Δ-plot for a single PM/MM probe pair in the presence of a second (or additional) PM/MM pair(s).

Discrimination is lowest in the presence of excess amounts of target because even the MM probe, while interacting more weakly with the target than the PM probe, will capture large amounts of target and generate a large signal. Conversely, discrimination is largest in the target-depleted regime: in the extreme case, a single target molecule would have to select the PM probe over the MM probe, producing infinite discrimination but at the expense of a very weak signal. Preferably, multiplexed analysis is thus carried out under conditions of slight target depletion so as to maximize discrimination while retaining an acceptable signal intensity to facilitate experimental measurements.

Figure 4A:
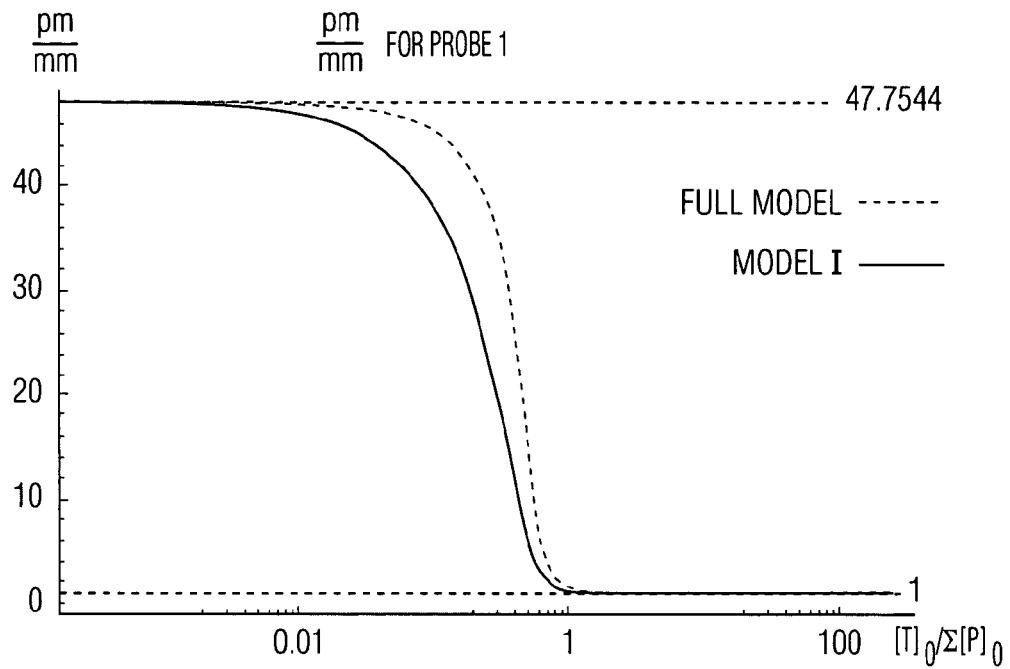
FIG. 4A plots PM/MM ratios of hybridization complexes with a target for the first pair of probes, as a function of the initial target concentration scaled by total (over all probes used under a given model in the multiplexed reaction) initial probe concentration, obtained under Model I (only the first pair of probes) and under Full Model (in the presence of the second pair of probes).
Figure 4B:
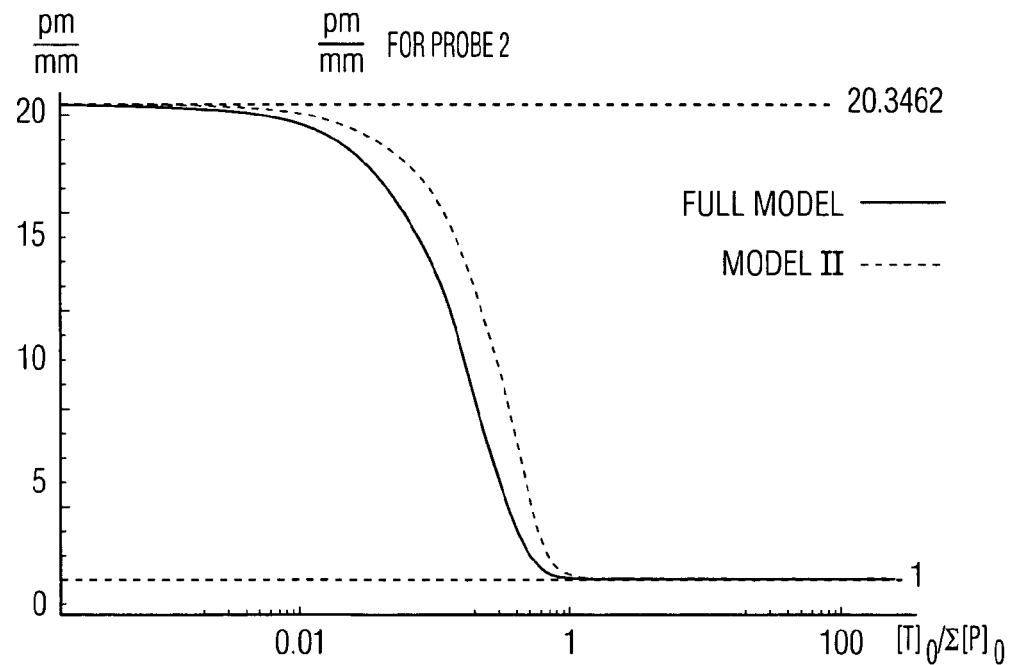
FIG. 4B plots PM/MM ratios of hybridization complexes with a target for the second pair of probes, as a function of the initial target concentration scaled by total (over all probes used under a given model in the multiplexed reaction) initial probe concentration, obtained under Model II (only the second pair of probes) and under Full Model (in the presence of the first pair of probes).
Figure 4C:
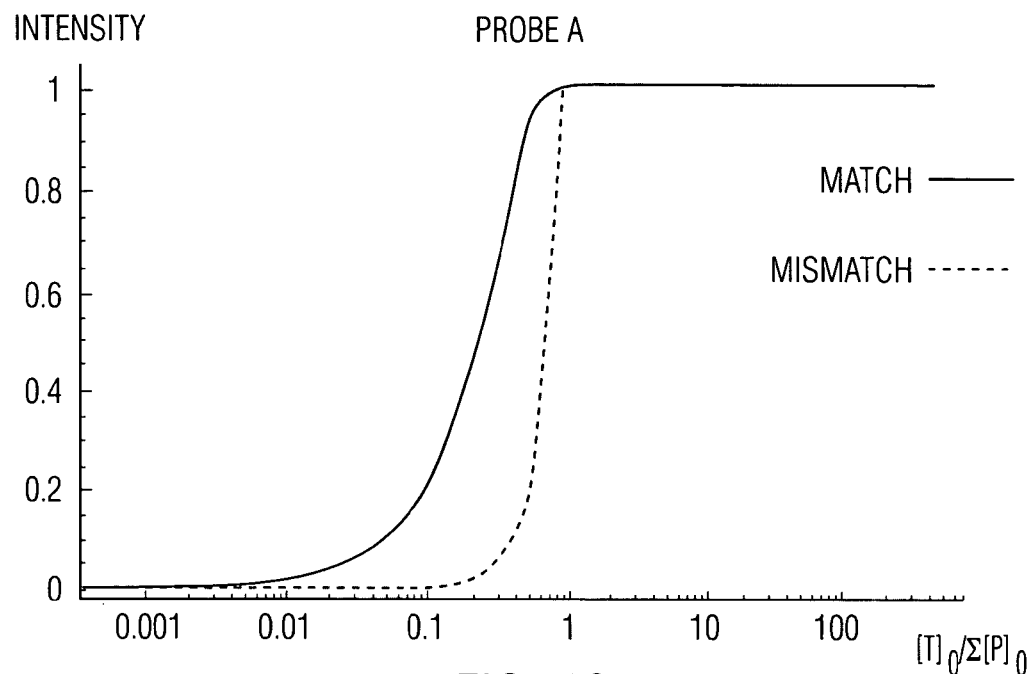
FIG. 4C shows the intensities of the probe pair of Model I of FIG. 4A, as functions of the initial target concentration scaled by total initial probe concentration.
Figure 4D:
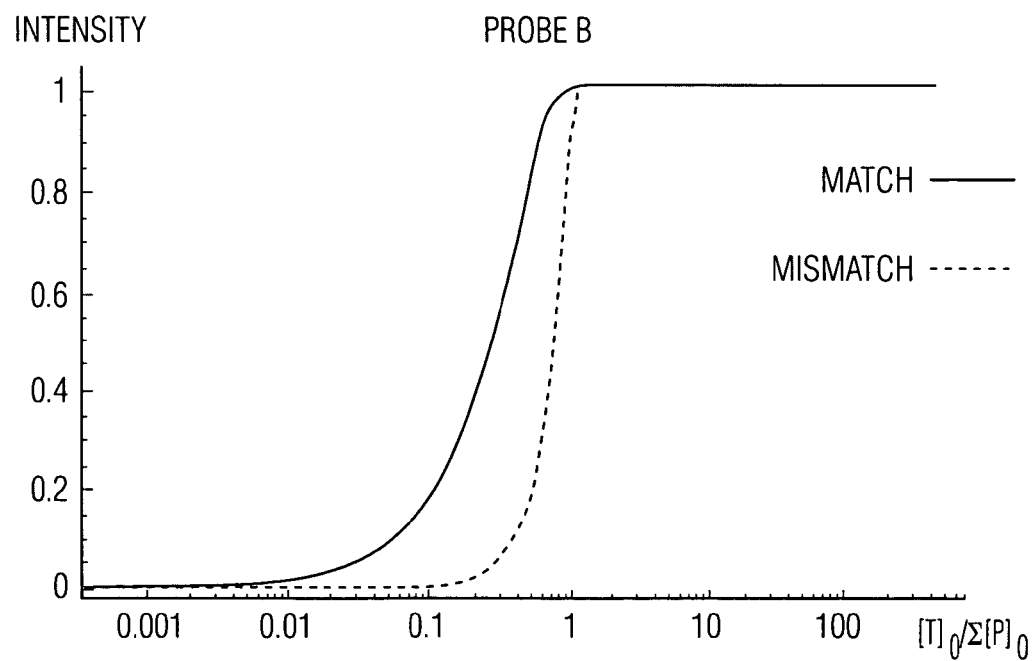
FIG. 4D shows the intensities of the probe pair of Model II of FIG. 4B, as functions of the initial target concentration scaled by total initial probe concentration.
Figure 4E:
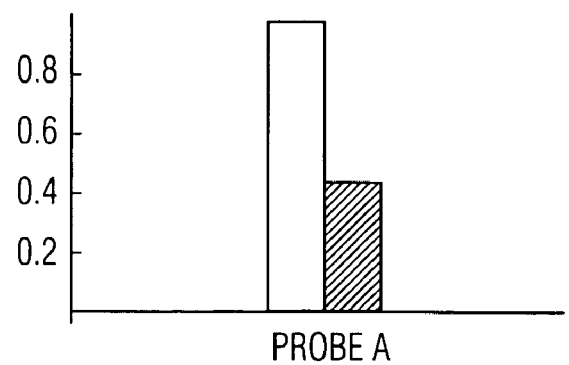
FIGS. 4E and 4F show, in bar graph form, where the X coordinate is taken at 0.7 from the graphs of FIGS. 4C and 4D, respectively, the normalized intensities for each probe pair A and B.
Figure 4F:
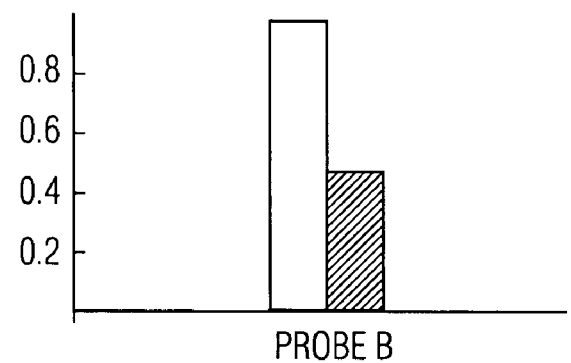
Figure 4G:
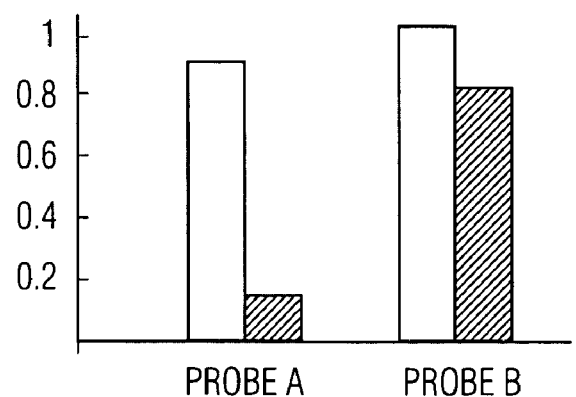
FIG. 4G shows, in bar graph form, the normalized intensities as in FIGS. 4E and 4F in a multiplexed reaction where both probe pairs A and B are present.

FIGS. 4A and 4B display the effects of competitive hybridization for a pair of PM/MM probes forming a complex with the same target, here Exon 11 of the CFTR gene, in accordance with the model of FIG. 2. FIG. 4A shows a shift "UP" of the Δ-plot of the first PM/MM pair (Model I) in the presence of the second PM/MM probe pair (Full Model), while FIG. 4B shows a shift "DOWN" of the Δ-plot of the second PM/MM pair (Model II) in the presence of the first PM/MM probe pair (Full Model). These Δ-plot shifts generally will have a dramatic effect upon the discrimination, A, attainable for a given initial molar ratio of target to probes. That is, the discrimination between perfect match and mismatch attained in an experimental design involving a single PM/MM probe pair for a given target can either improve, as in the case depicted in FIG. 4A, or deteriorate, as in the case depicted in FIG. 4B, with the addition of a second PM/MM pair directed to the same target.

Predicting the Effects of Competitive Hybridization

Figure 5A:
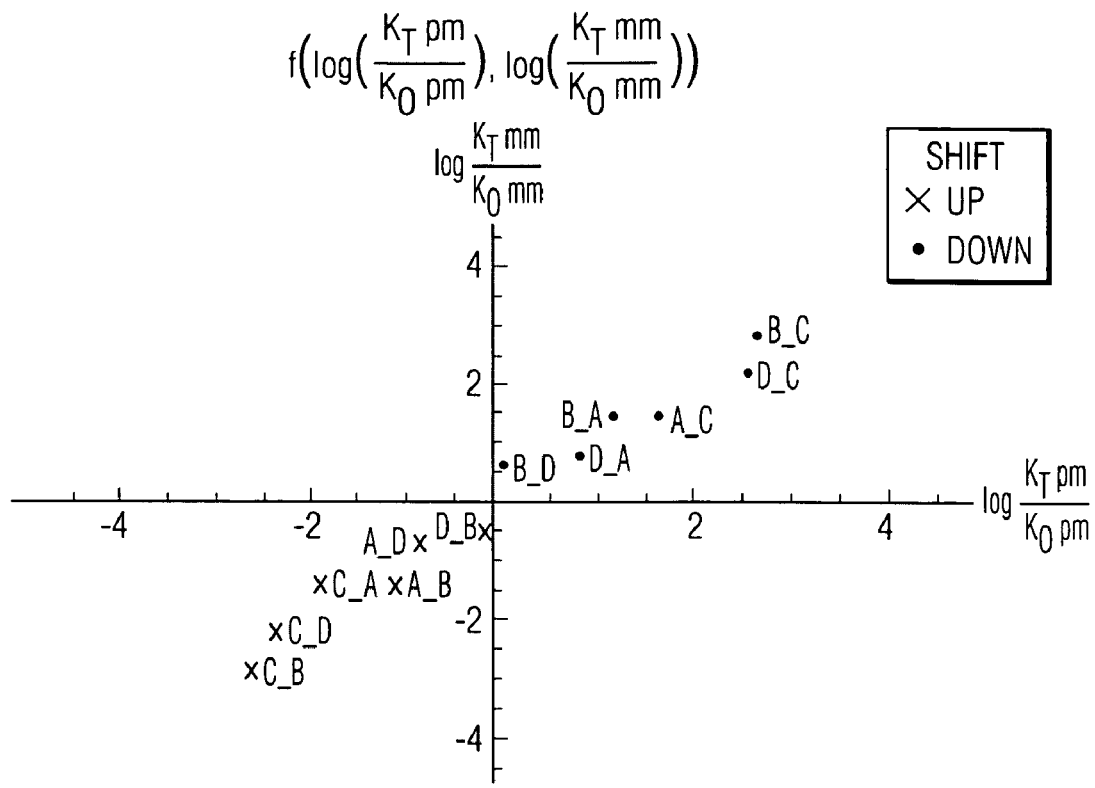
FIGS. 5A and 5B show a map indicating shifts in the plots of interaction strength between a target and a first PM/MM probe pair as a result of the presence of a second PM/MM probe pair
Figure 5B:
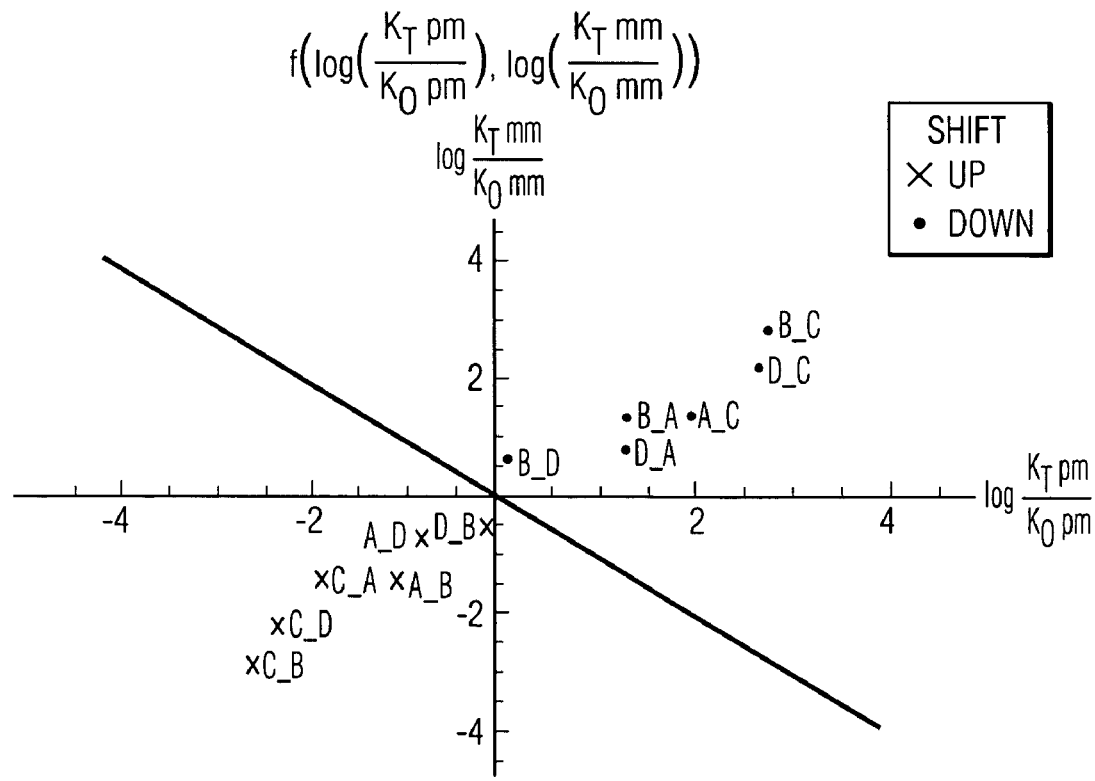

The methods described herein permit the prediction of the shifts in the Δ-plot, given the sequences of two or more PM/MM probe pairs. Consider two probes, each having associated with it the pair $\{P_{.,pm}, P_{.,mm}\}$. For each probe, the pm/mm ratio shifts up or down in the presence of the other probe. The direction of the shift was determined to be a function of the relative sizes of the affinity constants K, where cross-bound states can be neglected. For a given probe, let $K_T$pm, $K_T$mm denote the affinity constants for this probe's binding site with pm and mm, respectively; let $K_O$pm, $K_O$mm be the other probe's affinity constants with pm and mm. View the competition effect as a binary function on the space of affinity constants (+1 for up, −1 for down shift) and consider the projection of the affinity constant space $R^4=\{K_T\text{pm}, K_T\text{mm}, K_O\text{pm}, K_O\text{mm}\}$ onto the plane L with axes log $(K_T\text{pm}/K_O\text{pm})$ and $\log(K_T\text{mm}/K_O\text{mm})$. On this plane, the competition effect function values can be clearly separated by the line x+y=0. This condition holds for physical exon 11 CFTR probes, as shown in FIGS. 5A and 5B.

The empirically determined condition can be described by the following logically equivalent statements:

pm/mm ratio shifts up

↔y<−x

↔log($K_T$mm/$K_O$mm)<−log($K_T$pm/$K_O$pm)

↔$K_T$pm$K_T$mm<$K_O$pm$K_O$mm     (133)

Refer to the "empirical design rule" for comparison of a first pair of PM/MM probes (1) and second pair of PM/MM probes (2):

Δ(PM/MM Pair 1) increases in presence of PM/MM Pair 2 whenever $K_1^{PM}K_1^{MM}<K_2^{PM}K_2^{MM}$ Design of Optimal Probe Pairs for Competitive Hybridization The reliability in predicting Δ-plot shifts renders the empirical design rule, derived herein from the heuristic analysis described above, a valuable design tool to guide the selection of PM/MM probe pairs for multiplexed hybridization analysis under conditions permitting competitive hybridization. The predictive power can be applied to experimental designs as follows.

Suppose an application (e.g., HLA typing) requires the use of several (n) probes. Let the probes be ranked in order of importance to the problem: A, B, C, D, E, F . . . . One can choose the alternates for probes such that the ratios for important probes are improved. Recall that according to equation (133), the pm/mm ratio for this probe increases whenever $K_T$pm$K_T$mm<$K_O$pm$K_O$mm The process of selecting probes and alternates can be described in detail as follows. The DNA bases in an oligonucleotide are denoted by Σ={A, C, G, T}.

Start with probe A (most important); consider adding probe B. The options are:

Use probe B with alternate B' differing in:
Position 1, value EΣ−B[1];
Position 2, value εΣ−B[2];
. . .
Position N, value εΣ−B[N];
Do not use probe B.

(Note that, here, This probe=A; Other probe=B.)

Construction of Probe Pairs

Consider the three capture probes from the probe selection example above, designed for the analysis of mutations in exon 11 of the cystic fibrosis transmembrane regulator (CFTR) gene, where A=C381, B=A327, C=D359.

Pairwise computational analysis using the methods described herein above indicates that:
A327 will improve A(C381), the discrimination for C381;
D359 will improve A(A327), the discrimination for A327.

The empirical design rule herein identified indicates that it therefore follows that:
D359 will improve A(C381), the discrimination for C381.

Figure 7:
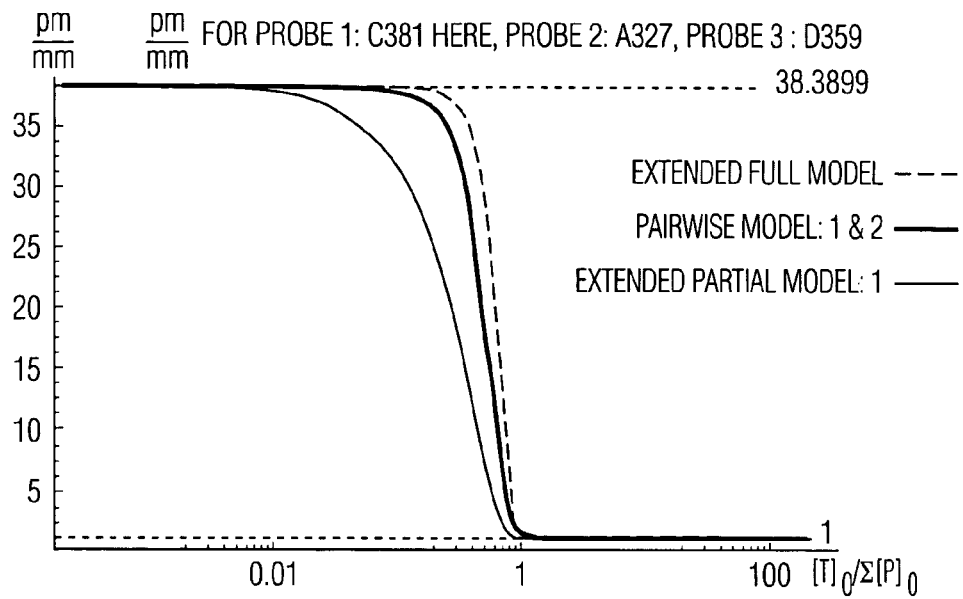
FIG. 7 shows plots of the ratio of the normalized discrimination for a first pair of PM/MM probes when allowed to hybridize alone, in the presence of a second pair of PM/MM probes, and in the presence of both second and third pairs of PM/MM probes forming hybridization complexes with a target, as a function of the ratio of the initial concentrations of target and all probes.

This prediction was tested by invoking the "extended model" for three probe pairs as described herein and comparing the resulting Δ-plots for the following cases (FIG. 7):

| | |
|---|---|
| Δ(C381) in presence of both A327 and D359 | right-most Δ-plot in FIG. 7 |
| Δ(C381) in presence of A327 only | middle Δ-plot in FIG. 7 |
| Δ(C381) only | left-most Δ-plot in FIG. 7 |

For a given initial target concentration, for example, corresponding to a value of 0.7 of the abscissa variable, Δ(C381) will increase upon addition of A327 and will increase further upon addition of D359.

Experimental Illustration of the Effects of Competitive Hybridization

Figure 8A:
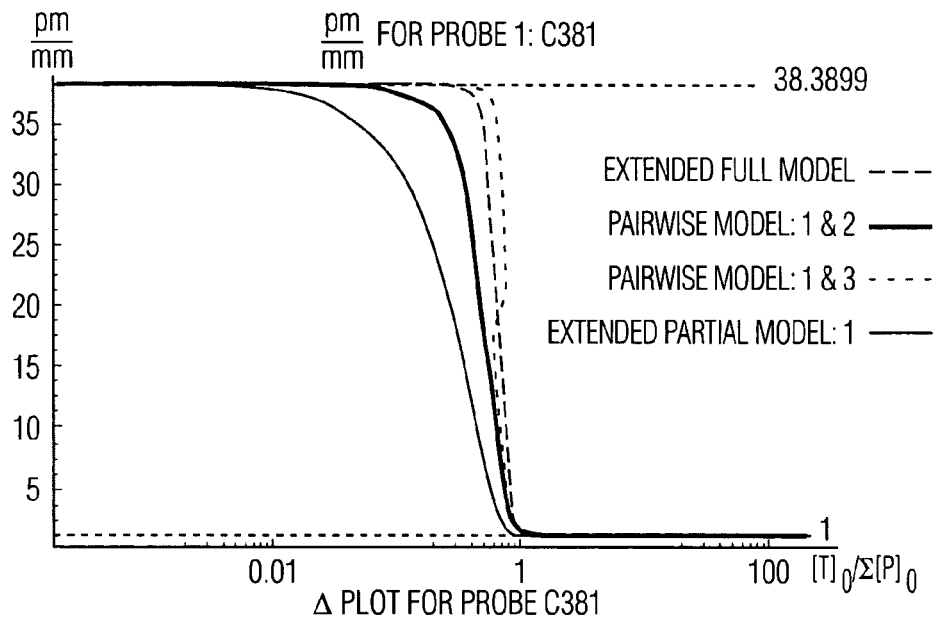
FIG. 8A shows the Δ-plots for probe C381, with probes A327 and D359 added.
Figure 8B:
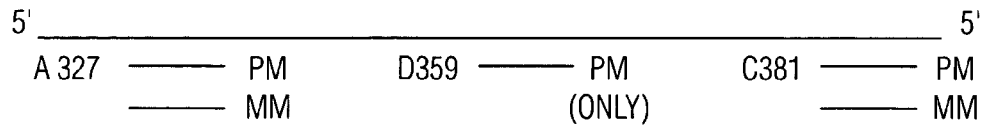
FIG. 8B shows the relative locations of the probes A327, C381 and D359 on exon 11.
Figure 8C:
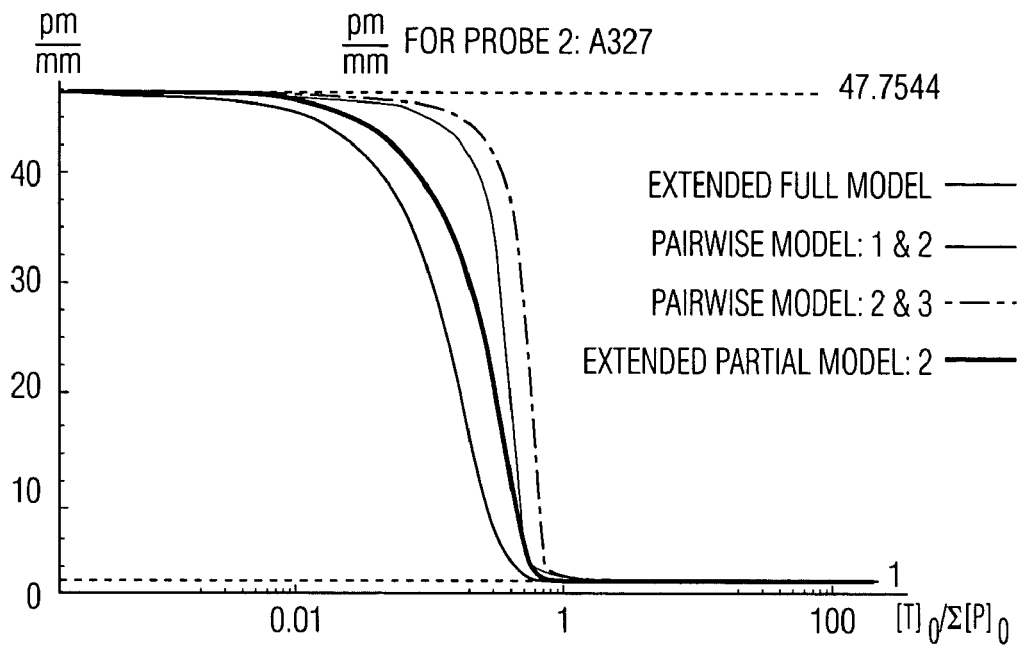
FIG. 8C shows the Δ-plots for probe A327, with probes C381 and D359 added.
Figure 8D:
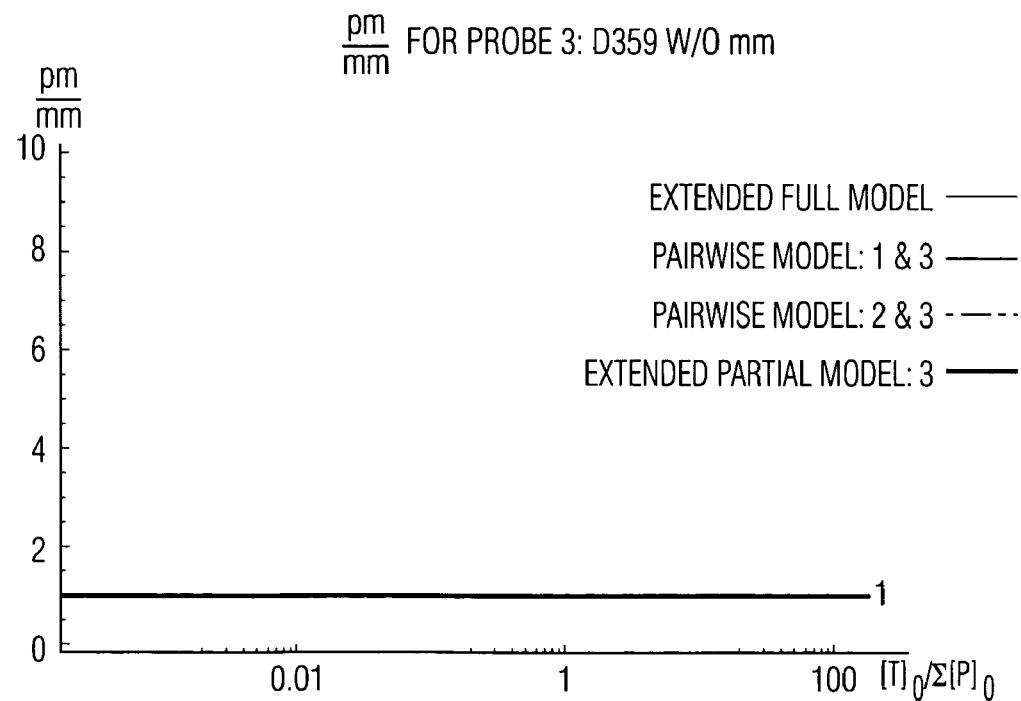
FIG. 8D shows that probe D359 shows no discrimination, as there is no mismatch D359 probe.

FIGS. 8A to 8D illustrate another potential application of the concept: introducing spurious "booster" probes into the multiplexed reaction for the sole purpose of improving the signal for probes of interest. FIG. 8A shows the results of hybridization of capture probes C381 to regions of the exon 11 of the cystic fibrosis transmembrane regulator (CFTR) gene in the presence of capture probes referred to as A327 and D359 (as depicted in FIG. 8B), when PM/MM probe pairs are present for A327 and C381, but only the PM probe is present for D359 (the "booster" probe in this example). The effect on the signal of probe C381 (as depicted in FIG. 8A) is analogous to that shown above (in FIG. 7): addition of probe A327 improves the signal for probe C381 (from "Extended Partial Model: 1" to "Pairwise Model: 1&2"), and further addition of "booster" probe D359 improves the signal for C381 even more (to "Extended Full Model"). The trade-off inherent in the empirical design rule shows that the signal for probe A327 (depicted in FIG. 8C, "Extended Partial Model: 2") deteriorates with the addition of probe C381 ("Pairwise Model: 1&2"). However, addition of "booster" probe D359 compensates for the deterioration, resulting in the improvement of the signal for probe A327 in the presence of both C381 and D359 ("Extended Full Model"). FIG. 8D shows that the "booster" probe D359 has no discrimination signal, regardless of which other probes it is multiplexed with, as expected, since no MM probe was included for probe D359. Nonetheless, since probe D359 is introduced as a spurious probe (i.e., its signal was never of interest), it fully serves its purpose as a "booster" probe by improving the signal of preceding probes.

This example illustrates that adding probes which bind competitively to the target can increase the signal generated if subsequent probes are chosen appropriately, demonstrating that the empirical design rule is borne out.

3—Probe Pooling

In some applications, such as mutation analysis (e.g., for CF), one does not have the freedom of choosing the sequence of the mismatch probe—"mutant" matching sequence is used as "wild-type" mismatch and vice versa. In those cases, the options listed above relating to selection of probes [appearing below the formula $K_T^{PM}K_T^{MM} < K_O^{PM}K_O^{MM}$] are reduced to:

Use probe B with the given alternate (dictated by "mutant" sequence), or

Do not use probe B.

Furthermore, there are applications where one cannot rank probes by importance—all probes are equally important. Hence, discarding a probe is not really an option. For these applications, one can easily extend the approach for selecting probes and alternates, described above, into a method for pooling probes, namely, sorting through equally important probes and separating them into groups of non-interfering probes. Starting with a randomly ordered list of n equally important probes, we go through the probe selection process (above), with the exception that whenever our method dictates that we discard a given probe, we use that probe to start a new "pool". Each subsequent probe gets placed by starting with the initial probe pool, and in the event it is to be "discarded" from it, cycles to the next available "pool". If all currently existing probe pools recommend that it be discarded, we use it to start a new "pool". In this manner, the original list of n probes gets separated into k groups, k<n.

One may also choose to adjust the selection criteria for a newly added probe to not only boost the signals of the existing probes in the pool, but also limit the decay of the signal for the newly added probe itself.

Experimental Results

FIGS. 9A-9E, 10A, and 10B show experimental results of combining probes and targets as shown in the figures, and as listed in the table in FIG. 9A. In FIG. 10B, adding the probe with the higher affinity (D359) together with the A327 probe to the target caused an increase in discrimination (panel C) as predicted by the empirical design rule. In FIG. 10A, adding the lower affinity probe (C381) together with the A327 probe to the target caused an increase in discrimination (panel C), which is opposite to the prediction of the empirical design rule. The results of various probe combinations in FIGS. 9A-9E are also not consistent with the empirical design rule. These inconsistencies indicate that the nearest neighbor model of affinity (used to calculate the affinity constants shown in the table in FIG. 6B) has limitations.

It should be understood that the examples, terms, expressions, and methods described herein are exemplary only, and not limiting, and that the invention is defined only in the claims which follow, and includes all equivalents of the subject matter of those claims.

What is claimed is:

1. A method of selecting a set of oligonucleotide probe pairs for use in a hybridization assay to determine the sequences at particular sites in a target sequence, wherein one member of a particular pair has a different sequence than the other member and wherein one member (the "PM probe") has a PM subsequence perfectly complementary to a normal, non-variant subsequence of the target sequence and the other member probe of that pair (the "MM probe") differs in sequence at a number of nucleotide positions from said one member and has an MM subsequence complementary to a known variant of said subsequence, and wherein different probe pairs have members including PM and/or MM subsequences which are complementary to different subsequences of the same target, and wherein the selection method is designed to maximize discrimination (where discrimination is determined from the ratio of the intensity of the signals generated from labels attached to the probes, a greater intensity of a signal of particular member probes indicating more of said particular member probes being annealed to said target) between members of a particular probe pair, when said target is annealed to two or more of said different probe pairs, the method comprising:

a) selecting a number of candidate probe pairs;

b) adding a first probe pair from said number of candidate probe pairs to the set;

c) adding additional probe pairs to the set if, for each successive probe pair to be added, said probe pair satisfies the inequality:

$$K_T^{PM} K_T^{MM} < K_O^{PM} K_O^{MM},$$

where: $K_T^{PM}$ is the affinity constant for the PM probe in the immediately-preceding-added probe pair binding to its designated target subsequence; $K_T^{MM}$ is the affinity constant for the MM probe in the immediately-preceding-added probe pair binding to its designated target subsequence; $K_O^{PM}$ is the affinity constant for the PM probe in the next successive probe pair binding to its designated target subsequence; and $K_O^{MM}$ is the affinity constant for the MM probe in the next successive probe pair binding to its designated target subsequence; and d) using the set of probe pairs obtained from step (c) in a hybridization assay to determine which of said target subsequences are normal and which are variant.

2. The method of claim 1 wherein the MM probe of the first and the additional probe pairs differ in sequence from the PM probe of each of said pairs by one nucleotide.

3. The method of claim 1 wherein the probe pairs are attached to encoded beads, wherein the encoding indicates the sequence of the attached probe.

* * * * *

SEQUENCE LISTING

```
<160> NUMBER OF SEQ ID NOS: 12

<210> SEQ ID NO 1
<211> LENGTH: 6
<212> TYPE: DNA
<213> ORGANISM: Artificial Sequence
<220> FEATURE:
<223> OTHER INFORMATION: Artificial Probe

<400> SEQUENCE: 1 cgaagt                                                                   6

<210> SEQ ID NO 2
<211> LENGTH: 6
<212> TYPE: DNA
<213> ORGANISM: Artificial Sequence
<220> FEATURE:
<223> OTHER INFORMATION: Artificial Probe

<400> SEQUENCE: 2 gcttca                                                                   6

<210> SEQ ID NO 3
<211> LENGTH: 17
<212> TYPE: DNA
<213> ORGANISM: Artificial Sequence
<220> FEATURE:
<223> OTHER INFORMATION: Artificial Probe

<400> SEQUENCE: 3
agttcttgga gaaggtg                                                      17

<210> SEQ ID NO 4
<211> LENGTH: 17
<212> TYPE: DNA
```

```
<213> ORGANISM: Artificial Sequence
<220> FEATURE:
<223> OTHER INFORMATION: Artificial Probe

<400> SEQUENCE: 4
agttctttga gaaggtg                                                  17

<210> SEQ ID NO 5
<211> LENGTH: 17
<212> TYPE: DNA
<213> ORGANISM: Artificial Sequence
<220> FEATURE:
<223> OTHER INFORMATION: Artificial Probe

<400> SEQUENCE: 5
ttattcacct tgctaaa                                                  17

<210> SEQ ID NO 6
<211> LENGTH: 17
<212> TYPE: DNA
<213> ORGANISM: Artificial Sequence
<220> FEATURE:
<223> OTHER INFORMATION: Artificial Probe

<400> SEQUENCE: 6
ttattcacgt tgctaaa                                                  17

<210> SEQ ID NO 7
<211> LENGTH: 17
<212> TYPE: DNA
<213> ORGANISM: Artificial Sequence
<220> FEATURE:
<223> OTHER INFORMATION: Artificial Probe

<400> SEQUENCE: 7
gagtggaggt caacgag                                                  17

<210> SEQ ID NO 8
<211> LENGTH: 17
<212> TYPE: DNA
<213> ORGANISM: Artificial Sequence
<220> FEATURE:
<223> OTHER INFORMATION: Artificial Probe

<400> SEQUENCE: 8
gagtggagat caacgag                                                  17

<210> SEQ ID NO 9
<211> LENGTH: 17
<212> TYPE: DNA
<213> ORGANISM: Artificial Sequence
<220> FEATURE:
<223> OTHER INFORMATION: Artificial Probe

<400> SEQUENCE: 9
gaggtcaacg agcaaga                                                  17

<210> SEQ ID NO 10
<211> LENGTH: 17
<212> TYPE: DNA
<213> ORGANISM: Artificial Sequence
<220> FEATURE:
<223> OTHER INFORMATION: Artificial Probe

<400> SEQUENCE: 10
gaggtcaatg agcaaga                                                  17
```

-continued

```
<210> SEQ ID NO 11
<211> LENGTH: 17
<212> TYPE: DNA
<213> ORGANISM: Artificial Sequence
<220> FEATURE:
<223> OTHER INFORMATION: Artificial Probe

<400> SEQUENCE: 11
tggtaatagg acatctc                                                      17

<210> SEQ ID NO 12
<211> LENGTH: 17
<212> TYPE: DNA
<213> ORGANISM: Artificial Sequence
<220> FEATURE:
<223> OTHER INFORMATION: Artificial Probe

<400> SEQUENCE: 12
tggtaataag acatctc                                                      17
```